United States Patent
Sy et al.

(12)

(10) Patent No.: US 6,528,269 B1
(45) Date of Patent: Mar. 4, 2003

(54) IMMUNOLOGICAL AGENTS SPECIFIC FOR PRION PROTEIN (PRP)

(75) Inventors: Man-Sun Sy; Pierluigi Gambetti, both of Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/204,816

(22) Filed: Dec. 3, 1998

Related U.S. Application Data

(60) Provisional application No. 60/090,165, filed on Jun. 22, 1998.

(51) Int. Cl.$^7$ ............... G01N 33/53; G01N 33/566; G01N 33/536; A61K 49/00; A61K 39/395
(52) U.S. Cl. .............. 435/7.1; 424/9.1; 424/130.1; 424/133.1; 424/134.1; 424/137.1; 424/138.1; 424/139.1; 424/141.1; 424/145.1; 436/501; 436/513; 436/536; 436/547
(58) Field of Search ............... 424/9.1, 130.1, 424/133.1, 134.1, 137.1, 138.1, 139.1, 141.1, 145.1; 435/7.1; 436/501, 513, 536, 547

(56) References Cited

U.S. PATENT DOCUMENTS 4,806,627 A * 2/1989 Wisniewski et al. ........ 530/387

FOREIGN PATENT DOCUMENTS

WO WO97/10505 * 3/1997 ......... G01N/33/543

* cited by examiner

*Primary Examiner*—Rodney P Swartz
(74) *Attorney, Agent, or Firm*—Fay, Sharpe, Fagan, Minnich & McKee, LLP

(57) ABSTRACT

The present invention is directed to a panel of monoclonal antibodies (Mabs) specific for murine prion protein $PrP^c$. These Mabs can be applied to immunoblotting, cell surface immunofluorescent staining and immunohistochemistry at light and electron microscopy. Additionally, these Mabs recognize both the normal ($PrP^c$) and protease-resistant ($PrP^{res}$) isoforms of PrP. Some Mabs are species restricted, while others react with PrP from a broad range of mammals including mice, humans, monkeys, cows, sheep, squirrels and hamsters. Moreover, several of the Mabs selectively recognize different PrP glycoforms as well as the metabolic fragments of $PrP^c$. These newly generated $PrP^c$ antibodies are useful for exploring the biology of $PrP^c$ and to establish the diagnosis of prion diseases in both humans and animals.

4 Claims, 15 Drawing Sheets

IMMUNOLOGICAL AGENTS SPECIFIC FOR PRION PROTEIN (PRP)

Priority of the present application is based upon U.S. Provisional Application No. 60/090,165 filed on Jun. 22, 1998 for "Monoclonal Antibodies Against Prion". This invention was made with Government support under Grant No. 642-2475 from The National Institute of Health. The United States Government may have certain rights to this invention.

This invention was made with government support under Grant No. NIH AGO8155 awarded by the National Institutes of Health. The government has certain rights in this invention.

FIELD OF THE INVENTION

The present invention is directed to a method for identifying prion protein which is involved in various transmissible neurological disorders of the central nervous system (CNS) in both humans and animals. Specifically, the method is based on the use of hybridomas or monoclonal antibodies (Mabs) and/or epitope binding fragments thereof prepared against prion protein in order to detect the presence of prion diseases. These antibodies or fragments thereof are suitable for use in highly sensitive immuno-assays for demonstrating the presence of prion protein. Additionally, the invention is also directed to pharmaceutical compositions containing the antibodies or fragments thereof.

BACKGROUND OF THE INVENTION

A prion is a small infectious protein. It is believed to be the cause of a number of degenerative neurological diseases. These prion caused diseases are collectively hereinafter referred to as "prion diseases".

Prions were formerly called "slow viruses" but are now known to be devoid of nucleic acids and are, therefore, neither viruses nor viroids. The name prion is a contraction of the terms protein and infection. Prions are resistant to inactivation by procedures that modify nucleic acids.

The membrane glycoprotein, now called prion protein (PrP), is involved in the pathogenesis of prion diseases. However, the normal function of PrP and its precise role in disease is not fully understood. It is believed that prion diseases are associated with alterations in PrP. The PrP gene is generally expressed at high levels in neuronal cells of the brain and at lower levels in other tissue such as the heart, lung and spleen. Furthermore, studies indicate that prion diseases are associated with a build up of PrP in and around cells of the brain.

Normal cellular prion protein is encoded by one single gene which can exist in multiple glycoforms with molecular masses existing between 27–40 K. Daltons. The glycoprotein is attached to the cell membrane of mammalian cells by a glycosyl phosphatidyl inositol (GPI) anchor.

Prion caused diseases, or transmissible spongiform encephalopathies (TSE), are neurodegenerative disorders that affect both humans and animals. Prion diseases are referred to as sponiform encephalopathies due to the characteristic of forming holes or pores in cranial tissue.

Development of prion disease may be the result of mutations in the PrP gene. Inherited prion diseases include; Creutzfeldt-Jakob disease (CJD), fatal familial insomnia (FFI) and Gerstmann-Straussler-Scheinker syndrome or disease (GSS) in humans. Prion diseases can also be contracted by an infectious mechanism. This group of diseases includes iatrogenic CJD and a new variant of CJD, which may be the result of transmission of bovine spongiform encephalopathy (BSE, also referred to as "Mad Cow" disease) from cattle to humans.

The majority of the prion diseases are sporadic disorders. The causes of these sporadic disorders are currently unknown (Parchi, et al., *Neurol.*, 8, 286–293 1995).

The prion diseases present in humans are generally present as a progressive dementia (impairment of intellectual functions) or ataxia (defective muscular coordination). In contrast, scrapie of sheep and bovine spongiform encephalopathy (BSE) are generally manifested as ataxia illness. Sheep and cattle possessing these forms of prion diseases lose their coordination and subsequently have to be destroyed.

The neuropathology of transmissible spongiform encephalopathies (TSE) typically comprises vacuolation of neuronal soma and of neurites and neuronal loss accompanied by reactive astrogliosis. The prognosis of patients having prion diseases is fatal.

Furthermore, the recent discovery of the transmission of bovine spongiform encephalopathy ("Mad Cow" disease) to humans raises an important health issue concerning the potential spreading of these fatal pathogens from domestic animals to humans. Therefore, there is a strong need for diagnostic agents to detect prion diseases and for therapeutic agents to inhibit infection.

Accumulated evidence suggests that the causative agent underlying prion diseases is a proteinaceous infectious pathogen that lacks nucleic acid (Prusiner, *Science.* 216, 136–144 1982). Prions differ from conventional bacteria, viruses, and viroids by their unique structure and properties. All prion diseases are believed to share the same basic pathogenic mechanism that involves the conversion of the normal cellular prion protein ($PrP^c$ or $PrP^{sen}$) into a form that is infectious, insoluble in non-ionic detergents and partially resistant to proteases ($PrP^{res}$ or $PrP^{sc}$). As mentioned above, $PrP^c$ is a cell surface protein anchored to the membrane by a GPI anchor.

Along these lines, $PrP^c$ and $PrP^{res}$ share an identical amino acid sequence. The conversion of $PrP^c$ to $PrP^{res}$ may involve a conformational change of $PrP^c$ from a predominantly alpha-helical form to a beta-sheet structure (Pan, et al., *Proc. Natl. Acad. Sci. USA*, 90, 10962–10966 1993). As a result, the difference between the normal form of PrP and the form associated with diseases may be solely conformational. (Notwithstanding the above, the accumulation within the central nervous system (CNS) of these abnormal $PrP^{res}$ in the brain is a cardinal feature of the prion disease pathology.)

The strongest evidence suggesting that $PrP^c$ is essential in the development of prion disease came from studies using $PrP^c$ "knock-out" mice which are devoid in $PrP^c$ and resistant to prion infection (Bueler, et al., Cell. 73, 1339–1347 1993). However, the conditions that trigger and determine the conversion of $PrP^c$ to $PrP^{res}$ remain unclear.

Experimental models of inherited prion diseases offer one approach to the study of the $PrP^c$ to $PrP^{res}$ conversion. Since many of the pathogenic mutations of the PrP gene ($PrP^M$) have high penetrance, it is likely that the change in $PrP^M$ metabolism plays an important role in determining the conversion of $PrP^M$ into $PrP^{res}$. Detailed studies on cell models of inherited prion diseases have underlined the complexity and the diversity of the metabolic changes affecting PrP (Peterson, et al., *J. Biol. Chem.*, 271, 12661–12668 1996).

The concept that TSEs are solely mediated by an infectious proteinaceous agent is not accepted by all investigators. It has been suggested that PrP functions as a cofactor and the development of prion diseases requires another infectious agent (e.g., a virus). Alper, et al., *Nature*. 214: 764–766 1967. Narang, *Proc. Soc. Exp. Biol.Mod.* 212: 208–224 1996. The prion hypothesis is also difficult to reconcile with two well established observations: one is the strain specificity of the prion protein and the other is the species restriction of disease transmission. The recent demonstration of the transmission of BSE to primates and mice raises the possibility that at least in some situations the infectious agent is able to surmount the species barrier. Lasmezas, et al., *Nature*. 381, 743–744 1996. Fraser, et al., *Vet. Rec.* 123: 472–477 1988. These observations suggest that the transmission of prion disease is a complex process which is still not fully understood.

One of the most puzzling observations in prion infected humans or animals is the lack of a robust inflammatory response during the progression of the disease. Neither humoral nor cell mediated immune responses against the prion protein have been detected in infected humans or animals. Earlier studies suggested that prion infection may result in suppression of the host immune function. Garfin, et al. *J. Immunology*. 120: 1986–1990 1978. The reasons that prions can evade recognition by the host immune system are not known. Accumulated evidence suggested that host animals may be tolerant to $PrP^c$ and $PrP^{res}$ derived from that species. In contrast to many other self proteins, the state of unresponsiveness to the prion protein is not overcome either by infection or by immunization with prion protein in Complete Freund's Adjuvant (CPA).

A few studies have provided indirect evidence that the host may be able to mount an immunological response against prion. By immunohistochemical staining, T lymphocytes have been observed in the early stages of scrapie (Manuelidis, et al., *Science*. 277: 94–98 1997). Several inflammatory responses, cytokines and chemokines have been reported to be present in the brain of infected animals (Campbell, et al. *J. Virol.* 68: 2383–2387 1994. Williams et al., *Brain Res.* 654: 200–206). Even if immunological responses can be detected in prion infected animals or in patients with prion diseases, the kinetics and magnitude of the responses are different from immune responses observed during infection with conventional microbial pathogens.

Indirect evidence indicates that the host lymphoid system is important in the transmission of prion diseases. In infected animals, the infectious prion protein is found in all components of the lymphoreticular system, including lymph nodes, spleen and Peyer's patches. (Fraser et al., *Nature* 226, 462–463 1970. Kimberlin, et al.,*J. Comp. Path.* 89 551–561 1979.) In mice, the infectious prion protein can be detected in the spleen as early as 4 days after intra-peritoneal or surprisingly, intracerebral inoculation. Therefore, propagation of the prion protein in the spleen appears to precede intracerebral propagation.

The important role that leukocytes play in prion disease is further supported by the observation that in vivo activation of the immune system is associated with a shortened incubation period in mice (Dickinson, et al., *Nature*. 272 54–55, 1978). Furthermore, mitogen activated murine T and B cells are 100 fold more susceptible to in vitro infection with prion protein than non-activated cells (Kuroda, et al. *Infect & Immunity*. 41, 154–161 1983). Mice with severe combined immunodeficiency (SCID) do not support propagation of the prion protein in the spleen (O. Rourke et al.,*J. of Gen. Virol.* 75: 1511–1514 1994). A recent study suggested that the dendritic cells in the lymphoid tissues may be the source of the infectious prion protein. In another study, it was reported that B cells are critical for disease propagation in mice. Mice lacking B cells are resistant to prion infection by the peripheral route.

In patients with nvCJD, large amounts of $PrP^{res}$ can be detected in the tonsil, an organ rich in antibody producing B cells. (Hill et al, *Lancet*. 49, 99 1997.) More recently, pathogenic PrP has also been reported to be present in the lymph nodes in the appendix of a patient with nvCJD, eight months prior to the onset of clinical disease. (Hilton, et al., *Lancet* 352, 703–704 1998.) These observations support earlier findings in animals that pathogenic PrP may accumulate in the lymphoid tissues prior to the development of clinical diseases in the CNS. Whether pathogenic PrP can be detected in other lymphoid tissues in humans has not been studied. Since transmission of both kuru and nvCJD are thought to be transmitted by ingestion of contaminated human tissue or beef, it is likely that the host mucosal immune system is involved in the transmission of these diseases.

While indirect evidence suggests a role for the host immune system in prion infection, the mechanisms by which lymphocytes participate in the establishment and/or propagation of prion diseases are not clear. Some studies suggest that peripheral scrapie infection may occur independently of the lymphoid cells. Alternatively, infection may be spread via the splanchnic complex, prevertebral ganglia or nerve endings in the preitoneal wall. (Aquzzi, *Lancet* 349: 742–743 1997.) (Kimberlin et al.,*J. Gen. Virol.* 67: 255–263 1989.) These pathways target the infection to the midthoracic spinal cord from which it spreads to the CNS and the brain.

Northern blot analysis revealed either the absence, or the presence of very low levels of $PrP^c$ mRNA in normal murine spleen. (Caughoy et al., *J. Gen Virol.* 69: 711–716 1988.) $PrP^c$ mRNA is present in murine B lymphocytic cell line and human T lymphocytic cell line. Cashman and colleagues were the first to report the presence of $PrP^c$ on normal human peripheral blood lymphocytes that may participate in lymphocyte activation. (Cashman et al., *Cell*. 61: 185–192 1990.)

However, the mechanism (or mechanisms) by which activated lymphocytes are more effective in promoting prion infection is not known. Progress in understanding prion biology and the pathogenesis of prion diseases has been hampered by the lack of a collection of immunological reagents.

A collection of well-defined monoclonal antibodies is essential for the diagnosis and understanding of many pathological conditions associated with prions. Moreover, the detection of prion diseases is not only dependent upon the availability of highly specific antibodies to PrP, but also antibodies which recognize PrP originating from a number of animal species. The need for a large panel of MAbs is even more critical since Western blotting and immunohistochemistry are the only reliable diagnostic procedures for identifying affected individuals and animals.

Currently, there is only one Mab, i.e. Mab 3F4, that reacts with PrP that has been extensively used to date (Kascsak, et al., *J. Virol.*, 61, 3688–3693, 1987). 3F4 is specific for human and hamster $PrP^c$. However, 3F4 does not recognize PrP from several animal species including mouse, cattle, sheep, monkey and squirrel. This is a significant limitation since transgenic mice are currently the widely used animal models for studying prion disorders. Additionally, Mab 3F4 does not recognize the C-terminal PrP$^c$ fragments which are generated during the normal metabolism of PrP or the pathological fragments containing the C-terminal region.

Furthermore, recent studies using PrP transgenic mice and PrP$^c$ "knock out" mice have dramatically improved applicants understanding of the pathogenesis of prion diseases. A Mab that can react with murine (i.e. mice and rats) PrP$^c$ will enhance an investigation ability to elucidate the mechanisms of disease propagation in these animals.

Additionally, 3F4 does not react with cattle or squirrel $PrP^c$. The potential of spreading of prion diseases from infected cattle or squirrel to human warrants the development of Mabs which will allow routine diagnosis and identification of infected animals.

Moreover, some metabolic products of $PrP^c$ are important in the pathogenesis of prion diseases. The epitope recognized by Mab 3F4 resides between amino acid 109 and 112. 3F4 does not react with the C-terminal PrP, a normally truncated fragment of $PrP^c$. 3F4 also does not react with all the other pathological fragments located at the C-terminal. Therefore, a panel of anti-PrP Mab recognizing different epitopes, spread allover the $PrP^c$ protein will facilitate the ability to detect and monitor the metabolic degradation and recycling of $PrP^c$.

Repeated attempts to generate more Mabs specific for murine $PrP^c$ in mice have not been successful. Williamson et. al. reported that immunization of PrP-/- mice with murine PrP in CFA resulted in a strong anti-PrP antibody response. (Williamson et al., *P.N.P.S.* 93: 7279–7282 1996.) However, these investigators were unable to generate any stable hybridomas. Another group was able to generate Mabs against human prion proteins using PrP-/- mice. (Krasemann et al., *Mol. Mod.* 2;725–734 1996.) These hybridomas were generated by immunizing the PrP-/- mice with DNA encoding the human prion protein. However, all the Mabs generated were specific for the N-terminal half of the prion protein.

Consequently, it is clear that understanding the biology of PrP and the pathogenesis of prion diseases requires an extensive library of well characterized antibodies to PrP. A collection of diverse Mabs would allow identification of the different metabolic products of $PrP^c$, $prp^M$ and $PrP^{res}$ providing new insights into the mechanism of prion conversion. Additionally, these Mabs would also be useful for investigating the involvement of activated lymphocytes in promoting prion infection. Ultimately, these Mabs and/or antibodies thereto will facilitate the diagnosis and/or treatment of prion diseases in humans and in animals.

SUMMARY OF THE INVENTION

Applicants have prepared a panel of Mabs specific for $PrP^c$ and $PrP^{res}$. These Mabs cross react with $PrP^c$ from other species of mammals including humans, monkeys, cow, sheep, hamster and squirrel. Some of the Mabs selectively recognize PrP metabolic fragments. Additionally, this panel also provides evidence that the $PrP^c$ expressed on peripheral blood lymphocytes (PBL) are quantitatively and qualitatively different from $PrP^c$ expressed in the brain. Therefore, this panel of Mabs is useful for characterizing and localizating normal, mutant and pathogenic PrP.

More particularly, the present invention is directed to monoclonal antibodies that specifically react with PrP which is involved in the formation of various neurodegenerative diseases. In addition, the invention is directed to the hybridoma cell lines which produce these antibodies. The invention allows for detection of the various forms of PrP using immunological methods comprised of monoclonal antibodies either in solution or in solid phase and specimens taken from a variety of tissue from different mammals.

Along these lines, the present invention is directed to the production of monoclonal antibodies specific for both normal cellular prion protein ($PrP^c$) and pathogenic prion protein ($PrP^{res}$), and the use of the monoclonal antibodies and associated hybridomas (fused myeloma-lymphocyte cells which produce the monoclonal antibodies) for diagnostic and/or therapeutic use. The monoclonal antibodies can be utilized for a variety of purposes, such as identifying, enumerating, localizing, and isolating PrP though a number of diagnostic means.

The invention also relates to the use of the specific monoclonal antibodies to examine the presence or absence of PrP and $PrP^{res}$ from tissues, e.g. brain, digestive organs, leukocytes, etc., from body fluids in mammals, and from urine and feces by immunoassay. The monoclonal antibodies of the present invention recognize PrP from multiple species including human, mouse, cattle, sheep and squirrel. Therefore, for the first time, it is possible to study and compare the expression of prion proteins from different animals.

Furthermore, since the monoclonal antibodies of the invention also react with sheep, bovine and squirrel PrP, these monoclonal antibodies are useful for diagnosing scrapie and BSE in infected cattle and squirrels.

In another aspect, the monoclonal antibodies of the present invention can distinguish different prion glycoisoforms in western blotting. This is particularly important since the degree, and the nature, of the $PrP^c$ glycoforms can modulate the pathogenesis of prion disease.

In an additional aspect, the monoclonal antibodies (and/or antibodies thereto) of the invention can be utilized with a variety of immunoassay and labeling techniques known to those skilled in the art, i.e. competitive and non-competitive assays, sandwich assays, etc. for diagnostic purposes.

In a further aspect of the invention, a diagnostic kit is provided for detecting prion proteins or antibodies thereto. The kit employs at least monoclonal antibodies of the invention and/or antibodies thereto.

In still another aspect, the invention provides monoclonal antibodies and/or antibodies thereto for treatment of prion diseases and/or for the development of therapeutic agents thereto.

DESCRIPTION OF THE DRAWINGS

The following is a brief description of the drawings which are presented for the purpose of illustrating the invention and not for the purposes of limiting the same.

FIG. 1 depicts analysis of a Western blot of human and mouse brain proteins immunoblotted with monoclonal antibodies 8H4, 5B2, and 6G9 to $PrP^c$. The following abbreviations are utilized: Prnp-/-, PrP knockout mice; H,I,U, diglycosylated, monoglycosylated, unglycosylated full-length Prp; I trunc and U trunc, monoglycosylated and unglcosylated truncated PrP, as indicated Mabs $8H^4$ and 6G9 react with all PrP forms while Mab 5B2 only reacts with the full-length forms, Mab 6G9 fails to recognize the diglycosylated forms. None of the Mabs react with any protein from the brain of PrP-/- mice which does not express PrP.

FIG. 2 depicts analysis of a Western blot of brain proteins from different mammals immunoblotted with monoclonal antibodies 8H4, 5B2, and 6G9 to $PrP^c$. The abbreviations are the same as those used in FIG. 1. The three Mabs react well with all species except the squirrel monkey, which is recognized poorly by both Mab 8H4 and 6G9 and the squirrel which is not recognized by 6G9. Both 8H4 and 6G9 but not 5B2 recognize the truncated forms in most species. Mab 6G9 fails to react with the H form in all species examined.

FIG. 3 is a diagrammatic representation of the epitope mapping of anti-PrP$^c$ monoclonal antibodies indicates the human PrP$^c$ residues 159 and 182, respectively, which correspond to 166 and 189, respectively, in the squirrel monkey.

FIG. 4 comprises a series of profiles of a FACScan analysis of expression of PrP$^c$ on the surface of a human neuroblastoma cell line which has been transfected with a PrP$^c$ gene. Clear areas represent staining of PrP$^c$-negative parental M17 cells. Shaded areas represent staining of PrP-positive transfectants with various anti PrP$^c$ monoclonal antibodies. Mab 582 stained less intensely than other Mabs.

FIG. 5 is a series of micrographs of the immunohistochemistry of PrP$^{res}$ in mouse brain (A), in a brain from a patient with CJD (B), and in a human neuroblastoma cell line transfected with a PrP$^c$ gene (C); FIG. 5A shows infected brain grafts from a transgenic mouse overexpressing PrP$^c$, Tg20 mice, implanted in the ventricular wall of a Prnp-/- mouse. Paraffin sections were processed and stained with monoclonal antibody 8H4. Mab 8H4 only stained neurografts (arrows) (X20); FIG. 5B shows cerebellar tissues from the brain of a patient with CJD were processed and stained with Mab 8H4. Plaque-like PrP deposits (arrows) are diffusely distributed in the molecular and granular layers of the cerebellum (X150); FIG. 5C shows a neuroblastoma cell line transfected with a construct expressing normal human PrP$^c$ stained with 8H4. PrP$^c$ is distributed in the intracellular compartment with a Golgi-like distribution (X430).

FIG. 6 consists of three photomicrographs of immunoelectron microscopy of PrP$^c$ transfected neuroblastoma cells; FIG. 6A indicates that gold particles line up the cell surface (X39,000); FIG. 6B shows the same gold particles line up the cell surface as FIG. 6A (X78,000); FIG. 6C shows gold particles distributed over the Golgi compartment (X59,000).

FIG. 7 comprises a series of profiles (i.e. graphs) of a FACScan analysis of two different neuroblastoma (M and V) cell lines, two astrocytoma (STT and CRT) cell lines and human PBL from a normal donor prepared and stained with anti-PrP Mabs, 8H4 (IgG$_1$), 6H3 (IgG$_1$), 6G9 (IgG$_1$) with clear areas representing staining profiles with irrelevant IgG$_1$ control antibodies and shaded areas representing staining profiles with anti-PrP Mabs.

Figure 12:
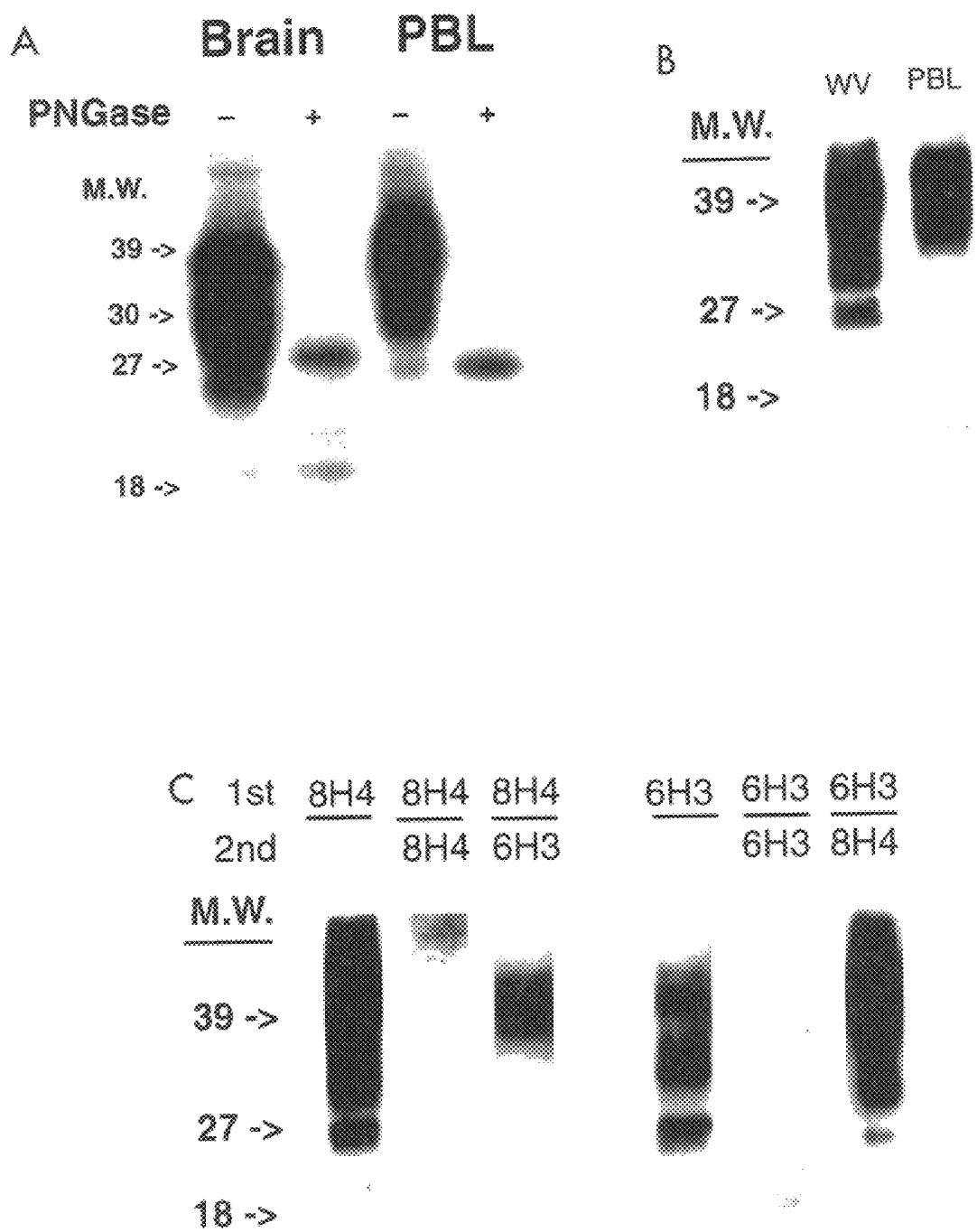

FIG. 12A is a photograph of a Western blot of total brain and human PBL proteins with anti-PrP Mab 8H4; FIG. 12B is a Western blot showing the immunoprecipitation of biotinylated cell surface PrP$^c$ from WV transfectant and normal human PBL; FIG. 12C is an SDS-PAGE gel showing immunoprecipitation of PrP$^c$ on WV transfectants with anti-PrP$^c$ Mabs.

Figure 13:
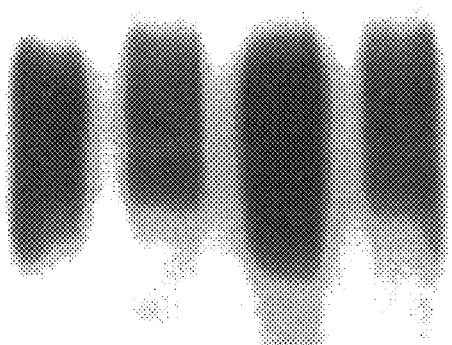
Figure 13:
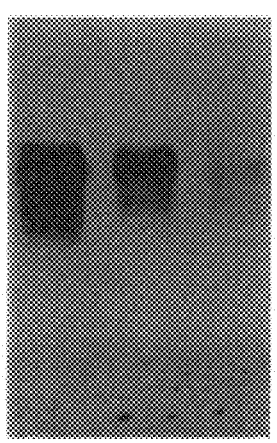
Figure 13:
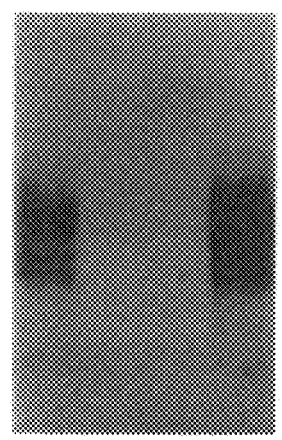

FIG. 13A is a photograph of a SDS-PAGE gel showing a Western blot of PrP$^c$ on normal and activated human PBL; FIG. 13B is an SDS-PAGE gel showing sequential immunoprecipitation of PrP$^c$ on activated human PBL.

Figure 14:
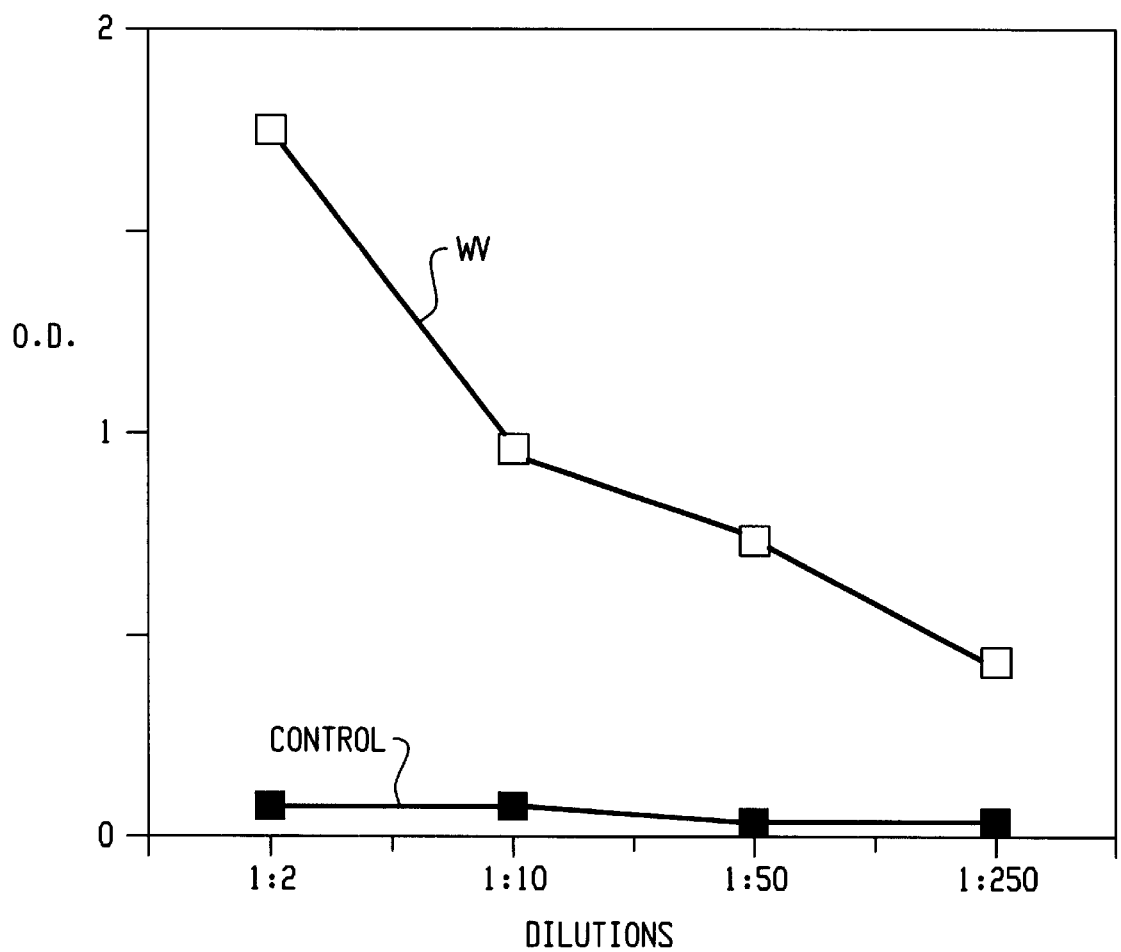

FIG. 14 shows the results of an ELISA for measuring soluble PrP$^c$.

Figure 15:
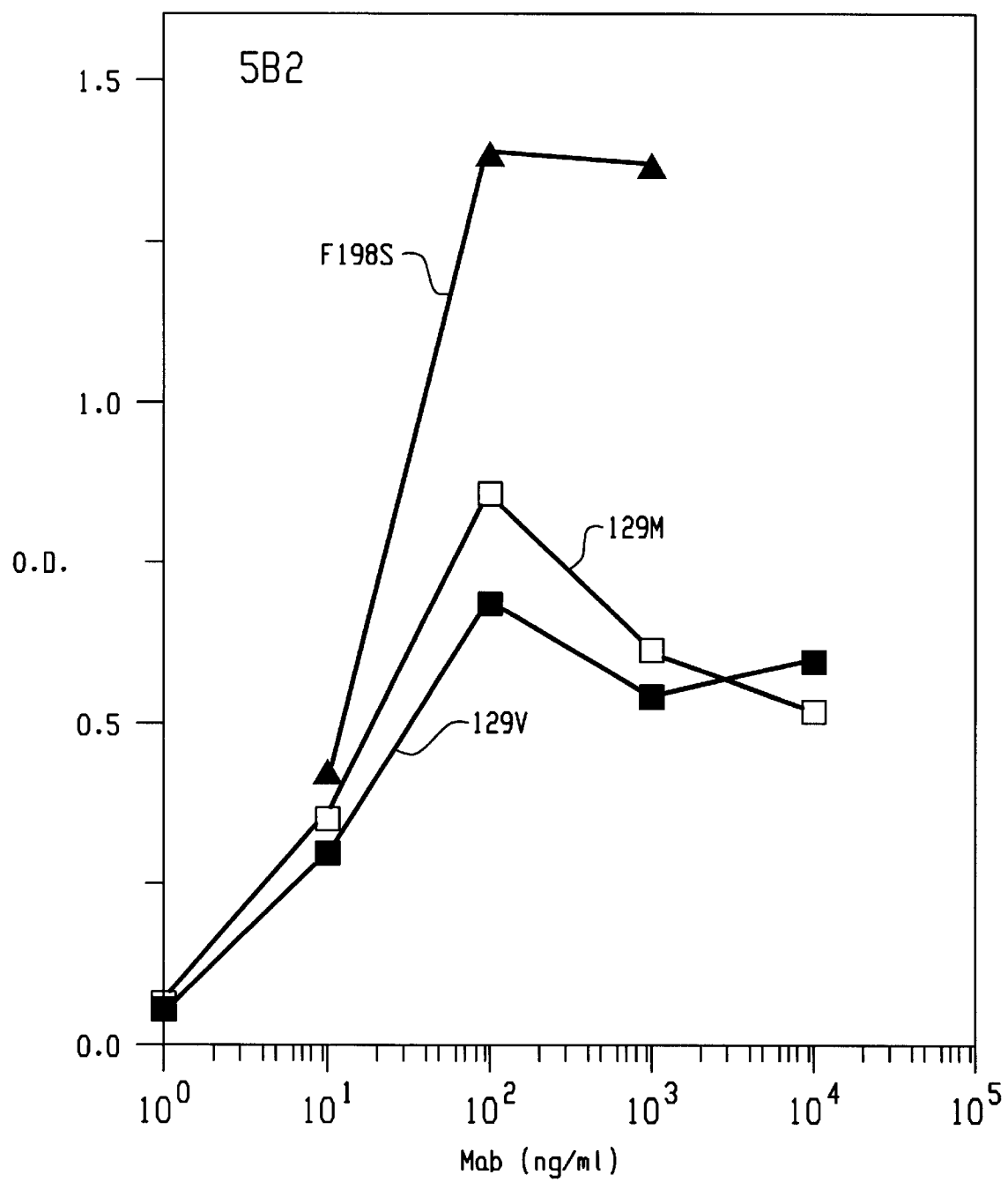

FIG. 15 shows the results of an ELISA for identifying pathogenic prion proteins.

DETAILED DESCRIPTION OF THE INVENTION

The objective of the present invention is to provide monoclonal antibodies, or epitope binding fragments thereof, with specificity for mammalian prion protein. The antibodies or fragments thereto are suitable for use in simple and highly sensitive immunoassays for detecting prion protein.

The present invention relates, in part, to the generation of a panel of monoclonal antibodies by immunizing prion "knock out" mice with recombinant normal mouse cellular prion protein (PrP$^c$). Spleen cells (antibody producing lymphocytes of limited life span) from the immunized mice were fused with non-producing myeloma cells (tumor lymphocytes that are "immortal") to create hybridomas. The hybridomas were then screened for the production of antibody specific to prion and the ability to multiply indefinitely in tissue culture. These hybridons were then propagated to provide a permanent and stable source for the specific monoclonal antibodies.

In particular, the present invention is directed to monoclonal antibodies to mammalian prion protein entitled 2F8, 5B2, 6H3, 8C6, 8H4 and 9 H7 and active fragments thereof. These monoclonal antibodies are produced by cell lines PrP2F8, PrP5B2, PrP6H3, PrP8C6, PrP8H4 and PrP9H7 respectively.

These monoclonal antibodies produced recognized not only human prion protein, but they also cross-reacted with prion proteins from mouse, cow, sheep and other species. These antibodies are believed to be the first panel of monoclonal antibodies that are capable of reacting with human, mouse, sheep and cow prion proteins.

The monoclonal antibodies of the invention can be used in Western blot, in immunofluorescent staining, immunohistochemistry, immunoelectron microscopy, and ELISA. A number of the monoclonal antibodies also recognize species restricted epitopes, while others react with several test animals. Western blotting of these monoclonal antibodies revealed that they recognize different epitopes on normal PrP$^c$. The monoclonals reacted differently to the PrP$^c$ glycoisoforms and to the fragments resulting from the metabolism of PrP$^c$. The monoclonal antibodies of the invention facilitate the investigation of the biology of PrP$^c$, and the progression and diagnosis of prion disease in both humans and animals.

The present invention also relates to the generation of a panel of Mabs which demonstrate that PrP$^c$ glycofoams an normal peripheral blood lymphocytes are different from the glycoforms expressed in normal brain tissue, on astrocytomas or on transfected nemoblastomas. Furthermore, the activation of lymphocytes resulted in quantitative as well as qualitative changes in the expression of PrP$^c$. There observations help explain why activated lymphocytes are more efficient in prion propagation.

I. Manufacturing Monoclonal Antibodies Specific for Prion

Generation of monoclonal antibodies which specifically react with murine PrP is facilitated by the use of a transgenic mammal (a mammal that contains some genetic material that has been experimentally transferred into it from other source or some genetic material that has been expermentally deleted) having an nonfunctional prion protein encoding gene (Prnp). Prnp is selectively knocked out by homologous recombination in the targeted mammal. It has been shown that transgenic (Prnp-/-) mice develop normally and are insusceptible to prion diseases due to the inability to form PrP (Manson, et al., *Mol. Neurobiol.*, 8: 121–127, 1994; B üeler, et al., *Nature*, 356: 577,582, 1992).

A suitable quantity of PrP is required for immunization of the transgenic mammal in order to form antibodies which specifically react with PrP. One way to produce suitable quantities of recombinant PrP is by transfecting *E. coli* with expression vectors carrying Prnp. Preferably, the cytoplasm of *E. coli* is transfected because it produces the largest quantities of PrP. The vector is designed to produce a large amount of stable mRNA that translates into PrP in the transfected cell. Prnp within the expression vectors can be derived from any mammal carrying that gene. This preferred method allows for the production of large quantities of PrP (Hornemann, et al., *FEBS Lett.* 413: 277–281 (1997). Alternatively, any other method can be used to produce sizeable quantities of PrP.

The transgenic (Prnp-/-) mammals are then immunized with PrP in CFA and boosted with PrP repeated in IFA. Shortly thereafter, somatic cells from the immunized Prnp-/- mammal, with potential for producing antibody, are fused with myeloma cells, forming a hybridoma of two cells by conventional protocol. Somatic cells may be derived from the spleen, lymph node, and peripheral blood of transgenic mammals. Myeloma cells which may be used for the production of hybridomas include murine myeloma cell lines such as MPCII-45.6TGI.7, NSI-Ag4/1, SP2/0-Ag14, X63-Ag8.653, P3-NS-1-Ag-4-1, $P_3X63Ag8U_1$, OF, and S194/5XX0.BU.1; rat cell lines including 210.RCY3.Agl.2.3; cell lines including U-226AR and GM1500GTGAl.2; and mouse-human heteromyeloma cell lines (Hammerling, et al. (editors), *Monoclonal Antibodies and T-cell Hybridomas IN*: J. L. Turk (editor) Research Monographs in Immunology, Vol. 3, Elsevier/North Holland Biomedical Press, New York (1981)).

Somatic cell-myeloma cell hybrids are plated in multiple wells with a selective medium, such as HAT medium. Selective media allow for the detection of antibodyproducing hybridomas over other undesirable fused-cell hybrids. Selective media also prevent growth of unfused myeloma cells which would otherwise continue to divide indefinitely, since myeloma cells lack genetic information necessary to generate enzymes for cell growth. B lymphocytes derived from somatic cells contain genetic information necessary for generating enzymes for cell growth but lack the "immortal" qualities of myeloma cells, and thus, last for a short time in selective media. Therefore, only those somatic cells which have successfully fused with myeloma cells grow in the selective medium. The infused cells were killed off by the HAT or selective medium.

A screening method is used to examine for potential anti-PrP antibodies derived from hybridomas grown in the multiple wells. Multiple wells are used in order to prevent individual hybridomas from overgrowing others. Screening methods used to examine for potential anti-PrP antibodies include enzyme immunoassays, radioimmunoassays, plaque assays, cytotoxicity assays, dot immunobinding assays, fluorescence activated cell sorting (FACS), and other in vitro binding assays.

Hybridomas which test positive for anti-PrP antibody are maintained in culture and may be cloned in order to produce monoclonal antibodies specific for PrP. Alternatively, desired hybridomas can be injected into a histocompatible animal of the type used to provide the somatic and myeloma cells for the original fusion. The injected animal develops tumors secreting the specific monoclonal antibody produced by the hybridoma.

The monoclonal antibodies secreted by the selected hybridoma cells are suitably purified from cell culture medium or ascites fluid by conventional immunoglobulin purification procedures such as, for example, protein A-SEPHAROSE hydroxylapatite chromatography, gel electrophoresis, dialysis, or affinity chromatography. FIG. 9 is a series of graphs showing the Mab 6H3 reactive epitope present on activated, but not normal, leukocytes from two different donors. The clear areas represent staining profiles with irrelevant $IgG_1$ control antibodies and the shaded areas represent staining profiles with anti-PrP Mabs.

II. Diagnostic Uses for Monoclonal Antibodies to PrP Diseases

For diagnostic applications, the antibodies of the invention typically are labeled with a detectable moiety. The detectable moiety can be any one which is capable of producing, either directly or indirectly, a detectable signal. By way of illustration, the detectable moiety may be a radioisotope, such as technicium, $^3H$, $^{125}I$, $^{35}S$, $^{32}P$, or $^{14}C$; a fluorescent or chemiluminescent compound, such as rhodamine, fluorescein isothiocyanate, or luciferin; or an enzyme, such as alkaline phosphatase, betagalactosidase or horseradish peroxidase. Any method known in the art for separately conjugating the antibody to the detectable moiety may be employed (Pain, et al., *J. Immunol. Meth*. 40:219, 1981).

In addition to mammalian tissue, the use of the monoclonal antibodies described herein can be extended to the screening of mammalian biological fluids for the presence of PrP. In vitro immunoserological evaluation of sera withdrawn from mammalian subjects thereby permits non-invasive diagnosis of prion diseases. For example, mammalian fluids, such as pleural fluids or the lymph, can be taken from a subject and assayed for PrP, either as released antigen or membrane bound on cells in the sample fluid, using the monoclonal antibodies in any known assay method, such as radioimmunoassays, competitive binding assays, sandwich assays, and immunoprecipitation assays.

Radioimmunassays use radioactivity in the measurement of antibody-PrP reaction. In such a method, the antibody is radio labeled and complexed with unlabeled PrP. The radiolabeled complex is then separated from unbound material by precipitation followed by centrifugation. Once the radiolabled antibody-PrP complex is separated from the unbound material, quantitation of the complex is measured by either the radiation directly or the effect that the radiolabel has on a fluorescent molecule, such as dephenyloxazole (DPO). The latter approach requires less radioactivity and is more sensitive. This approach, termed scintillation, measures the fluorescent transmission of a dye solution that has been excited by a radiolabel, such as $^3H$ or $^{32}P$. The extent of binding is determined by measuring the intensity of the fluorescence released from the fluorescent particles. This method, termed scintillation proximity assay (SPA), has the advantage of being able to measure antibody-PrP receptor binding in situ without the need for washing off unbound radioactive antibody from the particles.

Competitive binding assays rely on the ability of a labeled standard (which may be PrP or an immunologically reactive portion thereof) to compete with the test sample analyte for binding with a limited amount of antibody. The amount of test sample is inversely proportional to the amount of standard that becomes bound to the monoclonal antibodies. To facilitate determining the amount of standard that becomes bound, the monoclonal antibodies generally are insolubilized before or after the competition, so that the standard and analyte that are bound to the antibodies may conveniently separate from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex (David & Greene, U.S. Pat. No. 4,376, 110). The second antibody may itself by labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Typically, sandwich assays include "forward" assays in which the antibody bound to the solid phase is first contacted with the sample being tested to extract PrP from the sample by formation of a binary solid phase antibody-PrP complex. After a suitable incubation period, the solid support is washed to remove the residue of the fluid sample, including unreacted PrP, if any, and then contacted with the solution containing an unknown quantity of labelled antibody (which functions as a "reporter molecule"). After a second incubation period to permit the labelled antibody to complex with the PrP bound to the solid support through the unlabeled antibody, the solid support is washed a second time to remove the unreacted labelled antibody. This type of forward sandwich assay may be a simple "yes/no" assay to determine whether PrP or PrP$^{res}$ is present. Additionally, this assay may be made quantitative for comparing the signals generated by binding of PrP$^c$ and PrP$^{res}$.

Other types of sandwich assays, which may also be useful with PrP, are the so-called "simultaneous" and "reverse" assays. A simultaneous assay involves a single incubation step wherein the labelled and unlabelled antibodies are both added to the sample being tested at the same time. After the incubation is completed, the solid support is washed to remove the residue of fluid sample and uncomplexed labelled antibody. The presence of labelled antibody associated with the solid support is then determined as it would be in a conventional "forward" sandwich assay.

In the "reverse" assay, stepwise addition first of a solution of labelled antibody to the fluid sample, followed by the addition of unlabelled antibody bound to a solid support after a suitable incubation period, is utilized. After a second incubation, the solid phase is washed in conventional fashion to free it of the residue of the sample being tested and the solution of unreacted labelled antibody. The determination of labelled antibody associated with a solid support is then determined as in the "simultaneous" and "forward" assays.
Other Uses for Monoclonal Antibodies to PrP Diseases In addition to their diagnostic utility, the monoclonal antibodies of the present invention are useful for monitoring the progression of prion disease in a subject by examining the levels of PrP or PrP$^{res}$ in tissues on cells or serum samples over time. Changes in the levels of PrP or PrP$^{res}$ over time may indicate further progression of the prion disease in the subject.

The monoclonal antibodies of the present invention are potentially useful for targeting PrP or PrP$^{res}$ producing cells in-vivo. They can therefore be used in mammals for monitoring PrP conversion (i.e. from PrP$^c$ to PrP$^{res}$). For this application, it is preferable to use either affinity purified or humanized monoclonal antibodies. The purified monoclonal antibodies can be labeled with radioactive compounds, such as radioactive iodine, and administered to a patient intravenously. After localization of the antibodies at the site of PrP accumulation, they can be detected by emission tomographical and radionuclear scanning techniques.

Moreover, the monoclonal antibodies of this invention may be utilized in purified or humanized form for therapeutic applications. For therapeutic applications, the purified or humanized monoclonal antibodies are administered to a mammal in a pharmaceutically acceptable dosage form. The monoclonal antibodies are administered intravenously as one infusion or by continuous infusion over a period of time. The monoclonal antibodies may be administered by intraarticular, oral, intramuscular, topical, inhalation, subcutaneous, intrathecal, or intrasynovial routes. In addition to the monoclonal antibodies, the dosage forms possess pharmaceutically acceptable carriers that are nontoxic and nontherapeutic, including: serum proteins, buffers, ion exchangers, water, salts, electrolytes, sodium chloride, and the like.

The appropriate dosage of monoclonal antibodies will depend on the species of mammal, severity and course of disease, response to the monoclonal antibodies, and discretion of the physician. As stated above, the monoclonal antibodies may be administered to the subject at one time or over a series of treatments.

The following examples are offered by way of illustration only and are not intended to limit the invention in any manner. All patent and literature references cited throughout the specification are expressly incorporated.

EXAMPLE 1

Generation of Monoclonal Antibodies Specific for PrP

The creation of 129/Ola Prnp$^{-/-}$ mice follows the method described in detail in Manson, et al., *Mol. Neurobiol.* 8:121–127 (1994). Recombinant murine PrP$^c$ was prepared and purified as described in Hornemann, et al., *FEBs Lett.* 413:277–281 (1997). Prnp-/- mice were immunized with recombinant murine PrP (PrP$^c$) in Complete Freund's Adjuvant (CFA). After boosting the Prnp-/- mice three times with the corresponding antigen in Incomplete Freund's Adjuvant (IFA), spleen cells from one of the immunized Prnp-/- mice were fused with a myeloma, SP2/0, to create hybridomas using a conventional protocol (Harlow & Lane, *Antibodies; A Laboratory Manual* (Cold Spring Harbor Lab. Press, Plainview N.Y. (1988))). ELISA is used to screen for potential anti-PrP$^c$ monoclonal antibodies. ELISA plates were coated with 1 µg/mil of purified murine PrP$^c$ proteins overnight. Plates were then blocked with 3% BSA One hundred µl of culture supernatant was added to each well for 30 minutes at 37° C. After washing, a goat anti-mouse horseradish peroxidase-labeled Ig antibody (Amersham) was added for 30 minutes at 37° C. The reaction was visualized by 3,3',5,5' tetramethylbenzidine (Sigma) for 30 minutes at room temperature and blocked with 1 M sulfuric acid. Of the 1000 viable clones tested, 79 positive clones were identified in the first screening. In subsequent screening, 37 clones retained their specificity. Seven (7) of these clones (2F8, 5B2, 6G9, 6H3, 8C6, 8H4, 9H7) were chosen for further studies. Over time 6G9 has lost its activity. Six of these clones are produced by hybridoma cells deposited with the American Type Culture Collection (ATCC), Manassas, Va., on Feb. 12, 2002. These cells have been assigned ATCC Accession Nos, ATCC PTA-4065, ATCC PTA-4066, ATCC PTA-4067, ATCC PTA-4068, ATCC PTA-4069 and ATCC PTA-4070, respectively. The deposit was made in accordance with the terms and provisions of the Budapest Treaty relating to the deposit of viable microorganisms and was made for at least thirty (30) years and at least five (5) years after the most recent request for the furnishing of a sample of the deposit received by the depository, or for the affective term of the patent, whichever is longer, and will be replaced if it becomes non-viable during that period.

EXAMPLE 2

Interaction of Monoclonal Antibodies With PrP Expressed in Different Mammalian Species A. Immunofluorescent Staining Cultured, parental $PrP^c$ negative human neuroblastoma cell line M17 and a human neuroblastoma M17 cell line that was transfected with a normal human $PrP^c$ gene were harvested and washed with washing medium (Phosphate Buffered Saline supplemented with 5% New born calf serum, 0.1% $NaN_3$, pH 7.4) (Peterson, et al., *J. Biol. Chem.* 271:12661–12668 (1996)). A single cell suspension ($1\times10^6$/ml) was incubated with affinity purified monoclonal antibodies or an isotype control antibody on ice for 45 minutes. Cells were washed three times with washing medium and 25 µl Fluorescein isothiocyanate-conjugated Goat anti-mouse IgG antibody was added for 45 minutes on ice. Finally, samples were washed and fixed with 1% paraformaldehyde.

Cells were analyzed in a FACScan (Becton Dickinson, San Jose, Calif.). At least 5,000 cells were analyzed per sample.

B. Protein Studies and Immunoblotting for PrP from a Variety of Mammals

Brain tissue from different animals was homogenized in 9 vol of lysis buffer (100 mM sodium chloride, 10 mM ethylenediaminetetraacetic acid, 0.5% NP-40, 0.5% sodium deoxycholate, 10 mM Tris, pH 7.4, PMSF 2 mM). For deglycosylation experiments, samples were treated with N-glycosidase F (PNGase-F) (1000 units in 1% Nonident P40, 25 mM sodium phosphate pH 7.5) (Parchi, et al., *Ann. Neurol.* 38:21–29 (1995)). Proteins were separated in 12% polyacrylamide gels and then transferred to Immobilon P (Millipore) for 2 hours at 60 V. Membranes were incubated overnight at 4° C. with the different Mabs. The blots were developed with an enhanced chemiluminescence system (Amersham).

The monoclonal antibodies were separated according to the pattern of immunoreactivity with native and deglycosylated $PrP^c$ on immunoblots: monoclonal antibodies 8H4, 8C6, 9H7 and 2F8, recognize full length and truncated forms of $PrP^c$ Mab 5B2 reacts only with the full length $PrP^c$ and Mab 6G9 is glycosylation specific. Monoclonal antibody 6G9 selectively fails to recognize the highly glycosylated form of $PrP^c$. None of the monoclonal antibodies react with the brain homogenate from the $PrP^c$ mouse, confirming the specificity of all the Mabs for $PrP^c$.

Figure 1:
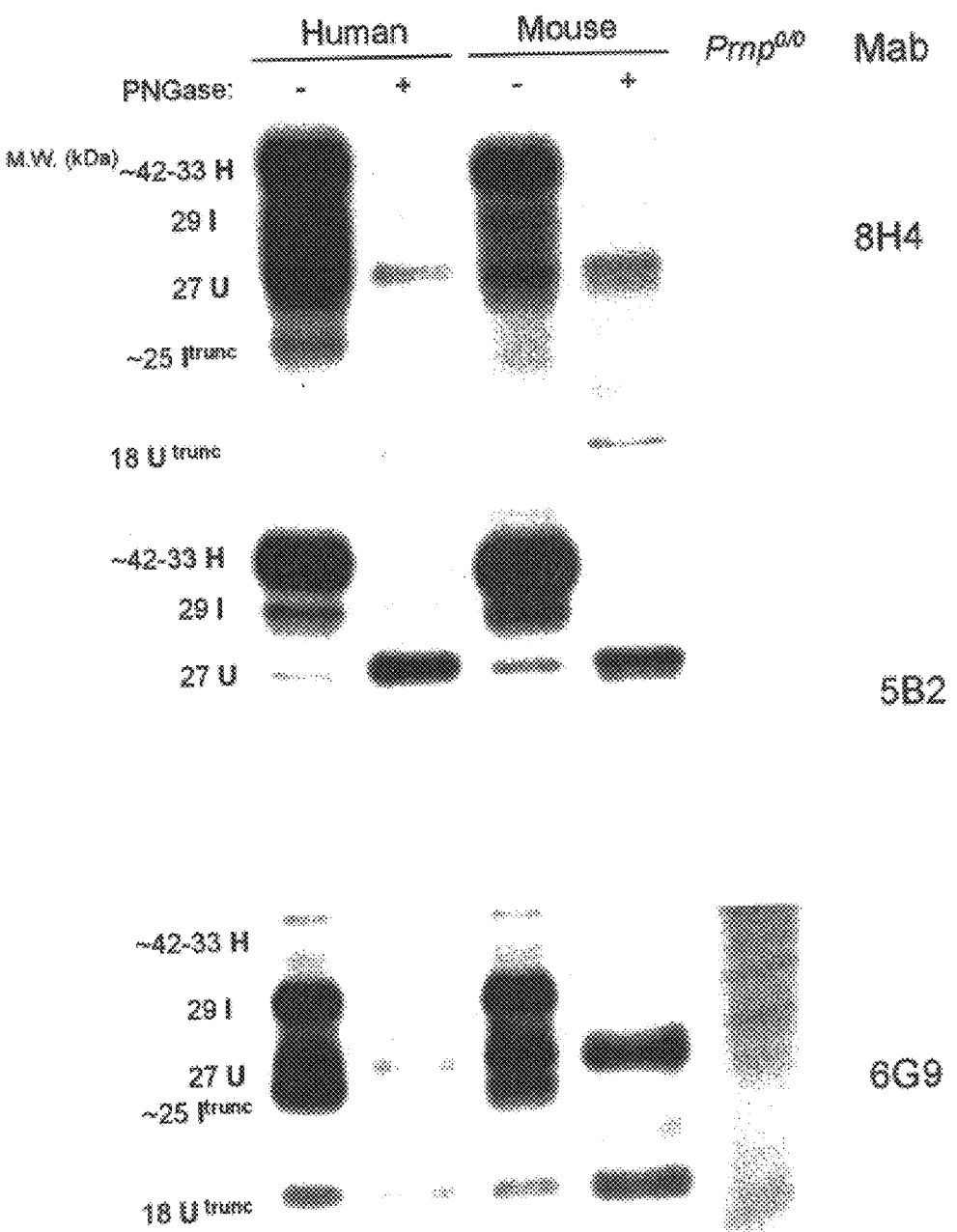

In humans and mice, Mab 8H4, representative of the first group, reacts equally with the three known $PrP^c$ glycoforms; the unglycosylated form which migrates at 27 kDa, the intermediate form, thought to be monoglycosylated which migrates at 28–30 kDa and the highly glycosylated forms which migrate as a band spanning 33–42 kDa (FIG. 1).

In addition, Mab 8H4 reacts with two bands at 25 kDa and 18 kDa, respectively. These two bands are known to contain the $PrP^c$ forms truncated at the N-terminus which are generated during normal processing of $PrP^c$. The 18 KDa protein is likely to be the unglycosylated form of the 25 KDa fragment, since, after deglycosylation, Mab 8H4 reacts only with the 18 KDa and 27 KDa proteins, the latter corresponding to the full length unglycosylated form. The only difference in Mab 8H4 immunoreactivity between human and mouse $PrP^c$ is the reduced affinity for the mouse 25 KDa fragment. Among the other Mabs of this group, 8C6 and 9H7 differ from 8H4 in the lack of immunoreactivity with the 25 KDa truncated form. Furthermore, Mab 2F8 has a weaker reaction with the full length forms and, in addition, fails to react with the truncated forms in the mouse (data not shown).

Mab 5B2 reacts strongly with the highly glycosylated and intermediate isoforms of human and mouse $PrP^c$ but reacts weakly with the unglycosylated isoform (FIG. 1). Mab 5B2 does not react with the truncated $PrP^c$ recognized by the previous group of Mabs. Mab 5B2 reacts strongly with $PrP^c$ after deglycosylation of $PrP^c$ with endoglycosidase-F (FIG. 1).

Mab 6G9 consistently failed to react with the highly glycosylated $PrP^c$ but reacts with all the other forms, including the truncated forms, from both humans and mouse (FIG. 1). Upon digestion with endoglycosidase-F, Mab 6G9 reacts with both 27 kDa and 18 kDa proteins (FIG. 1).

Figure 2:
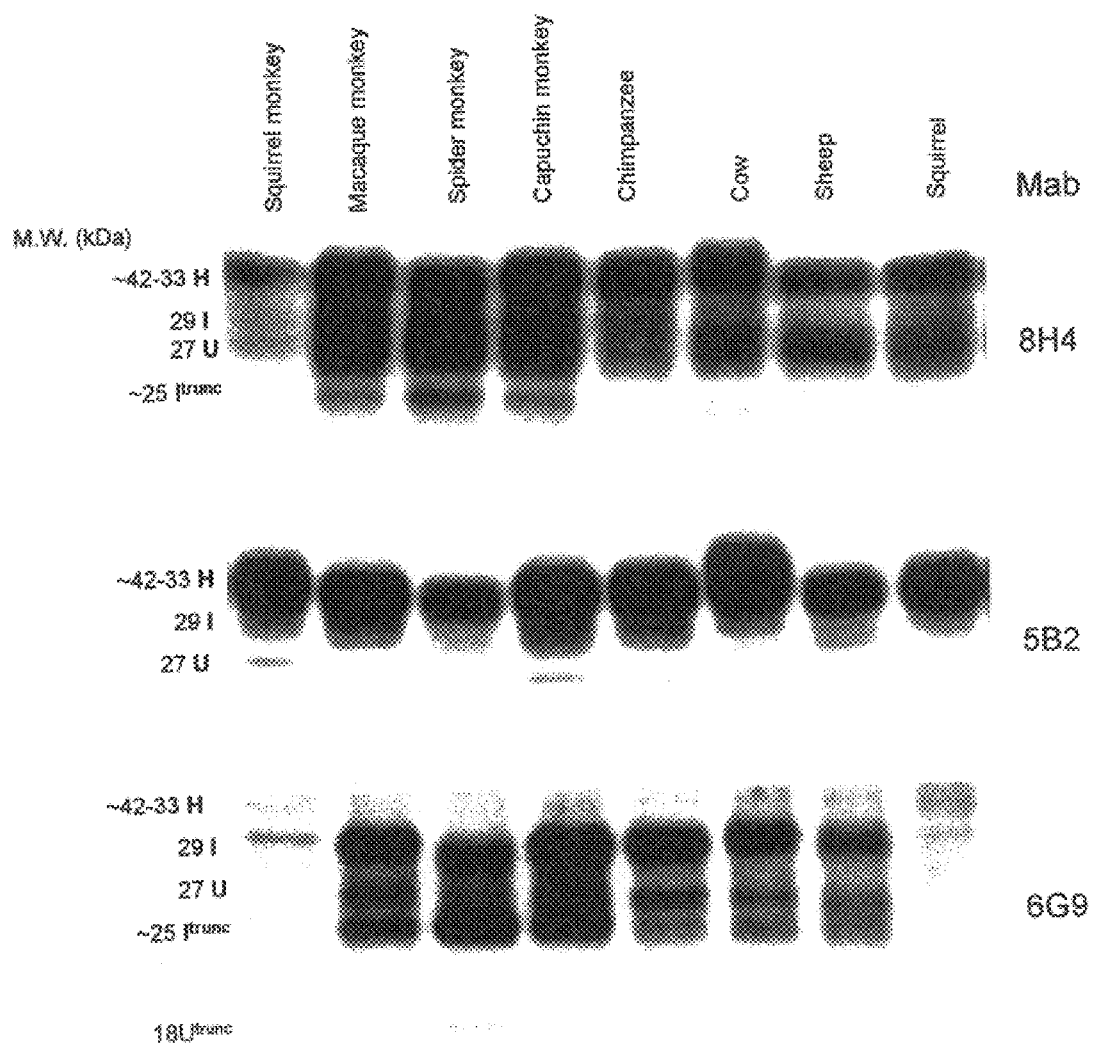

In the Macaque, Spider and Capuchin monkeys, Mab 8H4 from the first group reacts with the three full length glycoforms and the 25 kDa and 18 kDa truncated fragments similar to that observed in human and mice (FIG. 2). However, two additional, slightly different patterns can be seen in other animals. In the Chimpanzee, cow, sheep and squirrel, Mab 8H4 appears to react less with the intermediate form and the 25 kDa truncated form. In the Squirrel monkey, Mab 8H4 recognizes weakly the highly glycosylated $PrP^c$. Mab 2F8 recognizes $PrP^c$ from all the animal species studied reproducing a pattern which resembles that of Mab 8H4. Among the other Mabs of this group, 8C6 and 9H7 show a generally weaker and more species dependent reaction than 8H4. Mab 2F8 recognizes $PrP^c$ from all the animal species examined with a pattern similar to that of Mab 8H4 (data not shown).

Mab 5B2 shows a strong reactivity with all of the full length forms as in humans and mouse. However, Mab 5B2 appears to recognize the intermediate and the unglycosylated forms less well than the highly glycosylated form in the other species. Mab 5B2 does not recognize the truncated forms in any of the tested species (FIG. 2).

The distinctive characteristic of Mab 6G9 is the lack of a reaction with the highly glycosylated form in all species. Mab 6G9 also fails to react with $PrP^c$ from the Squirrel monkey and the squirrel. Moreover, in all species of animals tested Mab 6G9 recognizes the intermediate form as one band rather than two bands as demonstrated by the other Mabs (FIG. 2).

When the patterns of immunoreactivity of the Mab panel in the various species are compared, the overall immunoreactivity is higher with the human and mouse $PrP^c$ and lower with the squirrel monkey $PrP^c$ than with that of other species. As to the individual $PrP^c$ forms, the highly glycosylated form is generally well recognized by most of the Mabs across species, but there are differences in immunoreactivity for the intermediate, unglycosylated and truncated forms. These forms are well recognized in humans and less well recognized in cow, sheep, squirrel, Squirrel monkey and chimpanzee, perhaps because these forms are under-represented in these species. The mobility of the highly glycosylated and the intermediate forms are also heterogeneous. $PrP^c$ from cow and squirrel monkey migrate slower and $PrP^c$ from spider monkey faster than all other species because of the insertion or deletion in of one of the octapeptide repeats respectively.

Figure 3:
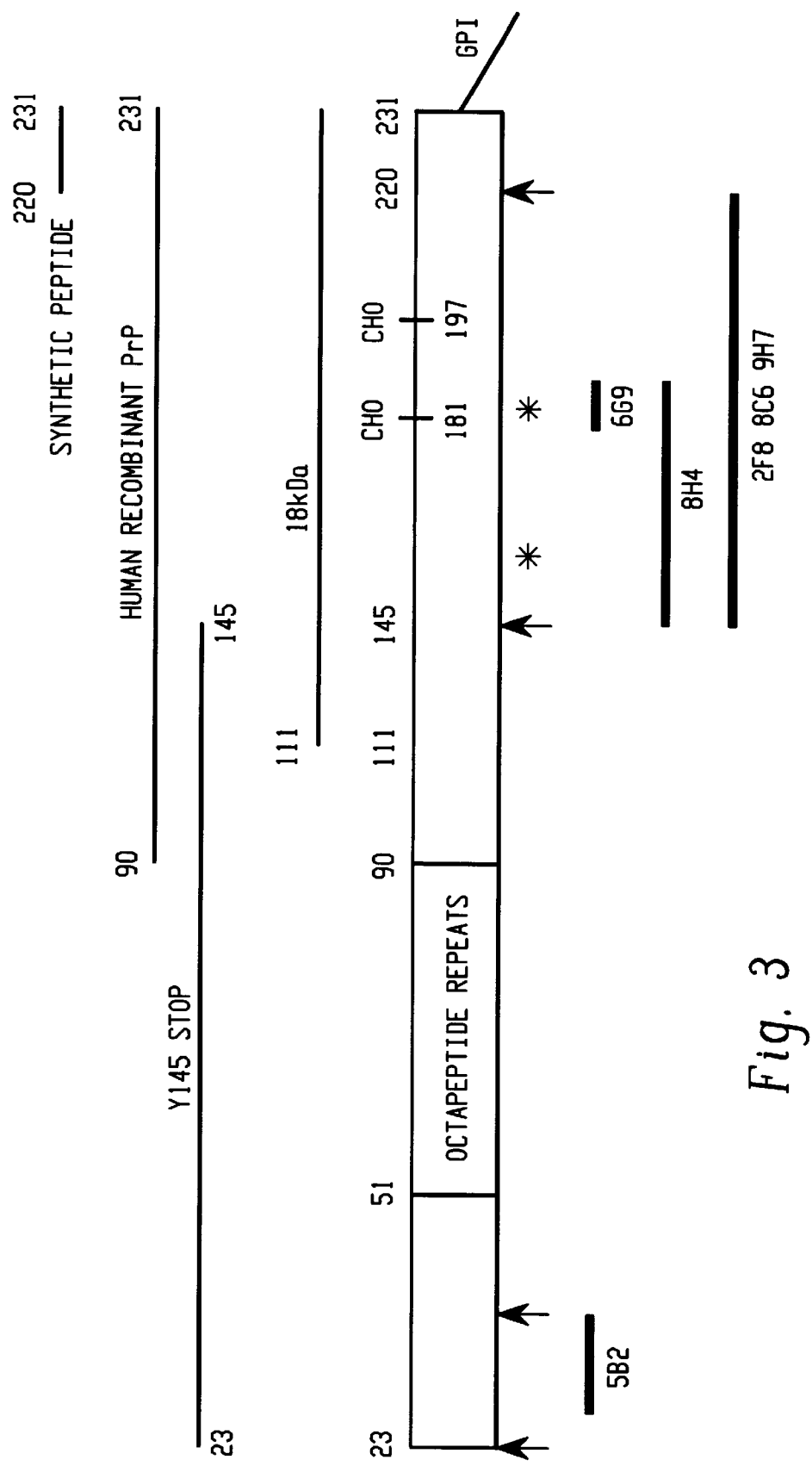

Mabs 8H4, 8C6, 9H7 and 2F8, the four Mabs of the first group must be directed to an epitope located in the C terminal region of $PrP^c$ between residues 145 and 220 (FIG. 3) for two reasons: 1) they react with the truncated $PrP^c$ forms which have been shown to be generated by the cleavage of the full length $PrP^c$ at amino acid 111/112 (Chen, et al., *J. Biol. Chem.* 270: 19173–19180 (1995)); and 2) they do not react with either the synthetic human PrP peptide 220–231 or with the mutant PrP expressed in neuroblastoma cells transfected with the 145 stop condon PrP gene construct which is truncated at residue 145 (Zanusso, et al., *Proc. Natl. Acad. Sci. USA* 95:8812–8816 (1998)). The epitope recognized by 8H4 might be further deduced by the lack of recognition of $PrP^c$ from squirrel monkey. Squirrel monkey carries two unique amino acid substitutions in the PrP sequence at residues 166 and 189.

Mab 5B2 does not immunoreact with the truncated $PrP^c$ forms and also fail to recognize the recombinant protein with a.a. 90-231 (Swietnicki, et al., *J. Biol. Chem.* 272:27517–27520 (1996)). Therefore, the epitope recognized by Mab 5B2 is reside at the N-terminal half, a.a. 23 to 90 of the molecule. This interpretation is supported by our recent finding that Mab 5B2 binds specifically to a synthetic peptide corresponding to a.a. 23-40 of the PrP.

The epitope bound by Mab 6G9 is most likely to reside at or very close to the N-glycosylation site that in humans is located at residue 181. This inference is based by on the finding that Mab 6G9 does not recognize the highly glycosylated $PrP^c$ form in which both glycosylation sites are occupied. The epitope localization at or close to human PrP residue 181 is further supported by the lack of reactivity of Mab 6G9 with all forms of $PrP^c$ from squirrel monkey. This $PrP^c$ carries an amino acid substitution at residue 189, corresponding to residue 182 in humans (Schatzl, et al., *J. Mol. Biol.* 245:363–374 (1995)).

C. Immunohistochemistry

Paraffin sections of infected brain grafts from a transgenic mouse overexpressing $PrP^c$ (Tg20) mice implanted in the ventricular wall of a Prnp-/-mouse were prepared. Sections were processed for immunostaining after hydrolytic autoclaving. The sections were deparaffinized, rehydrated and immersed in 98% formic acid for 1 hour at room temperature. Endogenous peroxidase was blocked by immersion in 8% hydrogen peroxide in methanol for 10 minutes. Sections were completely immersed in 1.5 mM HCL, and autoclaved at 121 C for 10 minutes. After rinsing, they were incubated with the different monoclonal antibodies. A goat anti-mouse Ig antibody and PAP was used to detect bound mouse monoclonal antibody (Sternberg, Meyer Immunochemical). Diaminobenzidine tetrahydrochloride was used to visualize the immunoreactivity. Paraffin sections from the brain of a patient with Creutzfeldt-Jakob disease (CJD) were processed and stained the same way.

Figure 4:
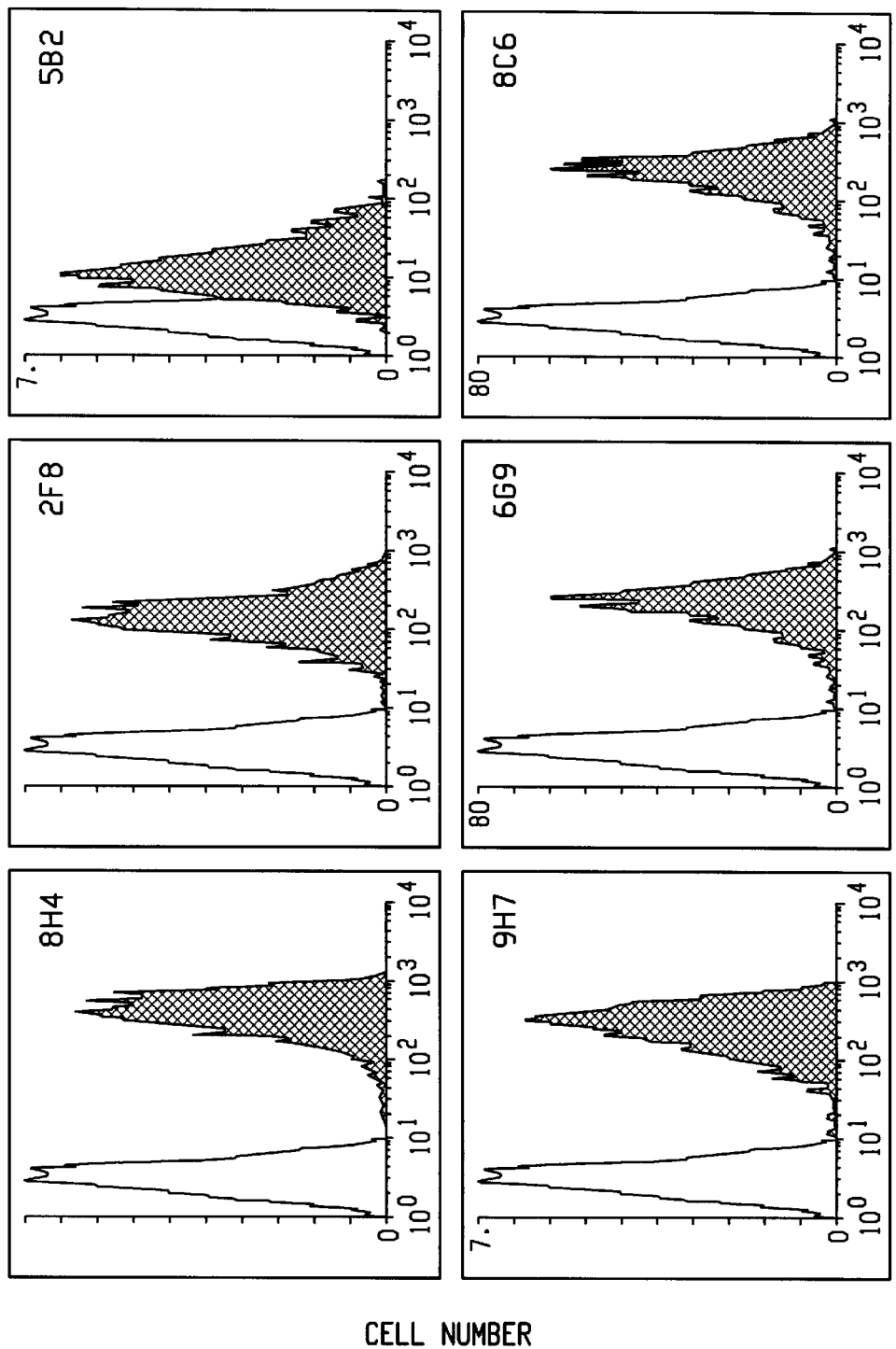

All six of the Mabs reacted with $PrP^c$ expressed at the surface of living human neuroblastoma cell transfectants overexpressing $PrP^c$. The fluorescenceactivated cell sorting (FACS) profiles of six of these Mabs are shown in FIG. 4. The staining intensity of Mab 5B2 is less than that of all the other Mabs suggesting that the epitope recognized by 5B2 may be less abundant. This observation is in good accordance with our earlier observation that Mab 5B2 does not recognize the truncated $PrP^c$ forms which can account for approximately ~30% of the total $PrP^c$ at the cell surface (Singh, Zanusso, Petersen, Gambetti, unpublished results). The same panel of Mabs did not stain the parental M17 cell line in which $PrP^c$ is not detectable.

Figure 5:
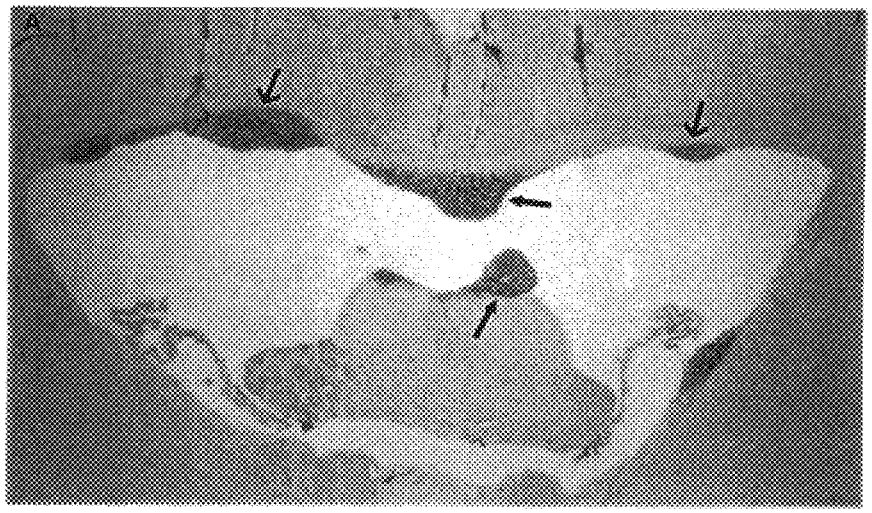
Figure 5:
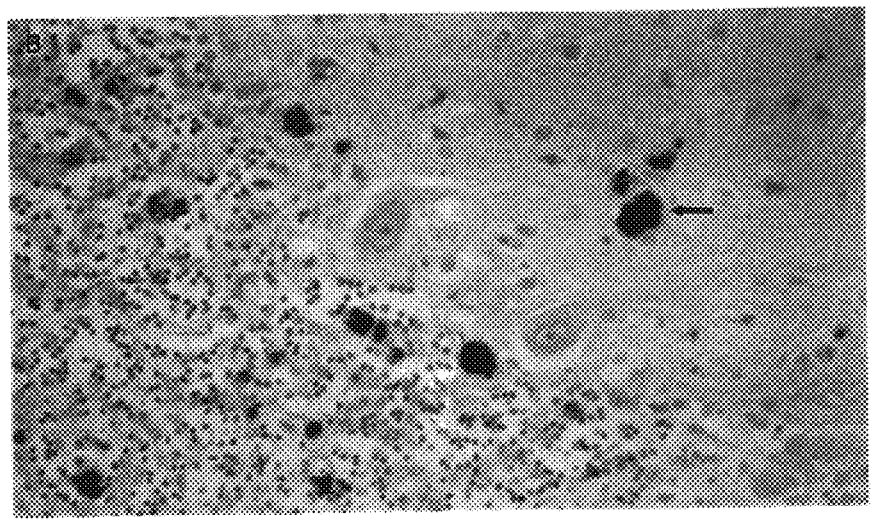
Figure 5:

Brain tissues from Tg2 O transgenic mice which had been implanted in Prnp$^{-/-}$ mice and then infected with $PrP^{sc}$ were processed and stained with Mab 8H4 (Bueler, et al., *Cell* 73:1339–1347 (1993); Brandner, et al., *Nature* (London) 379:339–343 (1996)). Mab 8H4 intensely immunostained the infected murine implants, especially their neuropil and the surface of neurons (FIG. 5A). A similar result was obtained with Mabs 2F8, 5B2, 8C6, 9H7 and 6G9 although the intensity of the staining of some of these antibodies was less than that of Mab 8H4. Applicants also stained tissue sections from fixed cerebellar cortex from a patient with Creutzefeldt-Jakob disease (CJD). All Mabs except for Mab 6G9 also immunostained $PrP^{sc}$ in the three cortical layers of the cerebellum in the affected CJD subject with a plaque-like pattern (FIG. 5B). These anti-$PrP^c$ Mabs did not stain unaffected regions of the brain. The procedures of hydrolytic autoclaving used to enhance staining of $PrP^{sc}$ may have destroyed the epitopes present in normal $PrP^c$. Furthermore, Mabs 8H4, 5B2 and 2F8 also react with the $PrP^c$ present in fixed and permeabilized neuroblastoma transfectants. (FIG. 5C). As reported earlier with another antibody, staining is seen in the cytoplasm and is most pronounced in the Golgi apparatus.

D. Electron Microscopy Immunohistochemistry

Neuroblastoma cell cultures (wild type/M) were fixed in 2.5% glutaraldehyde in 0.1 M phosphate buffer pH 7.4 for 90 minutes, washed in TBS (0.1M Tris pH 7.5, 0.15 M NaCl), scraped with a rubber policeman and then centrifuged at 500×g for 10 minutes at 4° C. The pellet was embedded in 1.5% agarose and cut in small oriented blocks under the light microscope using a razor blade. The floating blocks were immersed in 0.1% Triton X-100 in Tris Buffered Saline for 10 minutes, blocked with 10% non-fat dry milk for 30 minutes and incubated with the 8H4 monoclonal antibody (1:50) overnight at 4° C. in TBS, 0.1% Tween 20, 1% NGS, 1% BSA. The 8H4 Mab was omitted in negative controls. After washes in TBS the blocks were incubated with 5 nm gold conjugated goat anti-mouse IgG (Auro Probe™, Amersham) for 2 hours at RT. The blocks are then fixed in 2.5% glutaraldehyde and post-fixed in 1% $OsO_4$ for 1 h, dehydrated in alcohol and embedded in Spurr. Ultrathin sections were cut with a ultramicrotome (Ultracut FC4, Reichert Sci. Instrument), stained with uranyl acetate and lead citrate, and examined with a Jeol 100 electron microscope. For cryosections cells were fixed and scraped as above. Pellet was incubated in 30% polyvinylpyrrolidone and 2.3 M sucrose, placed on specimen stubs and frozen in liquid nitrogen. Ultrathin cryosections (approximately 120 nm-thick) were cut on glass knives in an ultracryomicrotome (Teichart ultracut S.

Leica Deerfield, Ill.). The sections were then placed on carbon and Formvar-coated grids and immunostained as described earlier.

Figure 6:
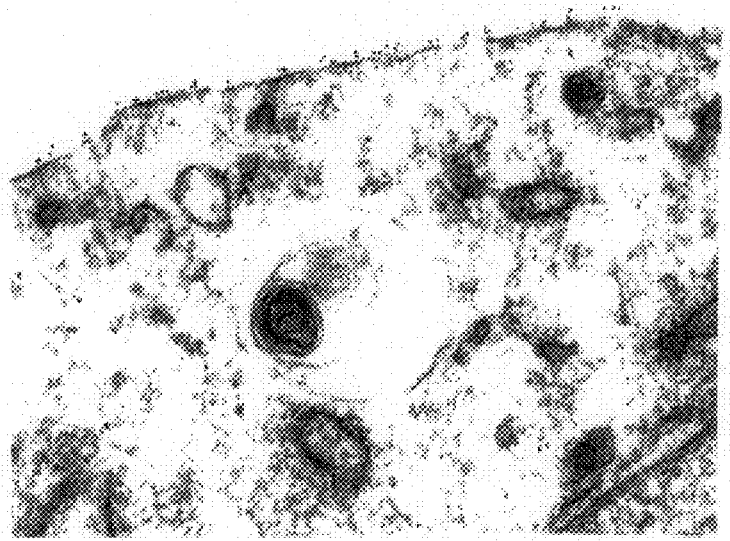
Figure 6:
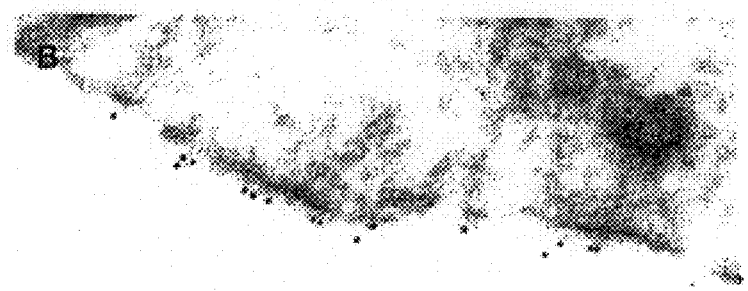
Figure 6:
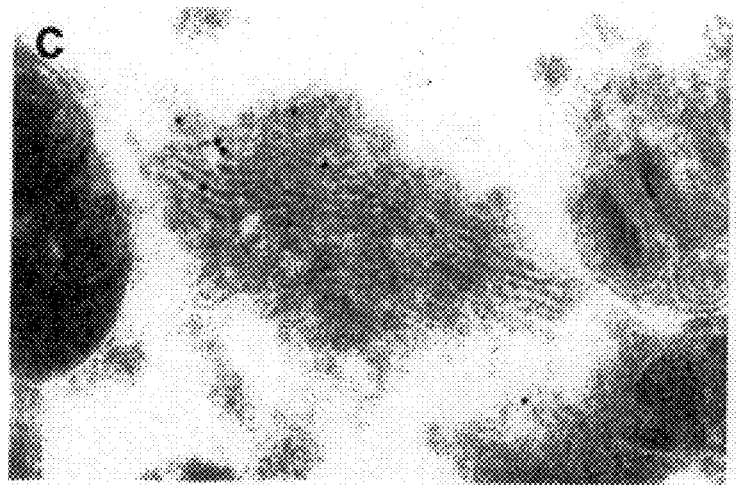

In order to identify the cellular organelle in which the conversion of $PrP^c$ to $PrP^{res}$ takes place, antibodies suitable for electron microscopic immunolocalization in well preserved cells and tissues were needed. Neuroblastoma transfectants were immunostained with Mab 8H4 and 5B2. Mab 8H4 immunolocalizes PrP$^c$ on the cell surface (FIG. 6A, 6B). Mab 5B2 labeled the Golgi compartment confirming applicants earlier observation using immuno-histochemistry (FIG. 6C).

Discussion

As mentioned above, immunochemical tests are the most efficient and reliable diagnostic procedures for identifying humans and animals affected by prion diseases. Only one Mab, 3F4, has been extensively used to date. It reacts with an epitope residing between amino acids 109 and 112. Mab 3F4 does not recognize the C-terminal PrP$^c$ fragments which are generated during the normal metabolism of PrP or the small pathological fragments containing the C-terminal region. Furthermore, Mab 3F4 detects PrP$^c$ in humans and hamster but not in mouse, cow, sheep, Capuchin monkey, and squirrel. This is a significant limitation since transgenic mice are currently the most widely used animal models for studying prion diseases. The ability to detect cow and squirrel PrP$^c$ will also help document the potential transmission of prion diseases from these animals to humans and will allow routine diagnosis of prion diseases in a number of mammals. Therefore, a panel of anti-PrP Mabs which recognize epitopes distributed over the PrP$^c$ will permit detection of PrP$^c$ and PrP$^{res}$ as well as monitoring of PrP$^c$ processing under normal or pathological conditions.

The Mabs raised in applicants study are directed to distinct epitopes throughout the 23-231 PrP$^c$ fragment. One of the Mabs, Mab 5B2, reacts with the N terminus of PrP$^c$. The remaining Mabs recognize the PrP$^c$ C-terminal fragments as well as other C-terminal fragments generated under pathological conditions.

Moreover, applicants Mabs also recognize PrP$^c$ from many different species of mammals including humans, mouse, cattle, sheep, squirrel, and hamster. Because applicants Mabs recognize PrP$^c$ from evolutionary diverse species, it is likely that these Mabs will also react with PrP$^c$ from other mammals. Applicants have shown that a single amino acid substitution might compromise the epitope recognition several Mabs; more frequently when the substitutions are not conservative. For example, Mab 6G9 selectively fails to recognize the squirrel monkey PrP$^c$ which is the only known mammal with a Val at PrP position 189 corresponding to the human Prp 182 residue. Thus, since 6G9 also fails to recognize PrP$^c$ in the squirrel, applicants can also predict the presence of an amino acid substitution at, or close to, the residue corresponding to the human residue 182 in this species whose PrP$^c$ has yet to be sequenced.

Some of the Mabs react differently with the various PrP glycoforms. One Mab, 6G9, preferentially recognizes the monoglycosylated and the unglycosylated forms but not the highly glycosylated forms. In contrast, another Mab 8H4 recognizes all three isoforms equally well in humans and Macaque, Spider and Capuchin monkeys, but only two glycoforms from cow, sheep, and squirrel. These antibodies will be useful in comparing glycoforms in different species and in identifying the individual glycoforms under conditions in which they are altered.

The study of PrP$^c$ metabolism and the PrP$^c$ to PrP$^c$ conversion has been impaired by the difficulty to identify cellular locales of PrP$^c$ processing and conversion. All of the Mabs applicants developed are suitable for immunohistochemistry of PrP$^c$ and PrP$^{res}$ on fixed and unfixed tissues. More important, applicants have been able to use immuno-electron microscopy with Mabs 8H4 and 5B2 to demonstrate the presence of the prion protein on the cell surface and in the Golgi apparatus of neuroblastoma cells fixed in glutaraldehyde. The ability to conduct ultrastructural immunolocalization following glutaraldehyde fixation is especially critical. Glutaraldehyde is the fixative of choice for electron microscopy but commonly cannot be used in immunocytochemistry because such treatment denatures the epitopes. Thus, the Mabs of the present invention should provide an opportunity to map the ultrastructural distribution of the PrP$^c$ and PrP$^{res}$ on fixed and unfixed tissues.

EXAMPLE 3

Interaction of Monoclonal Antibodies With Human Lymphocytes Expressing PrP

A. Monoclonal antibodies and cell lines and normal human peripheral blood leukocytes An expression plasmid coding for human PrP$^c$ with methionine at residue 129 was transfected into M17, a PrP$^c$ negative neuroblastoma cell line, to establish M17-M. Another expression plasmid coding for PrP$^c$ with valine at residue 129 was transfected into M17 to establish M17-V (Petersen, et al., *J. Biol. Chem.* 271: 12661–12668 (1996)). STT and CRT are astrocytoma cell lines derived from two patients with grade IV astrocytoma. These two cell lines were provided by Dr. R. M. Ransohoff of Cleveland Clinic Foundation, Cleveland, Ohio. The octapeptide repeat deletion construct (Δ8) was created by oligonucleotide directed loop-out mutagenesis to remove the octapeptide repeats. The deletion was confirmed by sequencing. Normal human peripheral blood leukocytes were obtained from normal donors by isolation over Ficoll-Hypaque density gradients. Normal PBL were activated in vitro with 5 μg/ml of PHA at 2.5×10$^6$ cells/ml in RPMI medium supplemented with 10% FCS, 1% L-glutamine and 1% antibiotics for 48 to 72 hours. After culture, lymphocytes were repurified with Ficoll-Hypaque step gradients.

NBHAc25 is a CD4$^+$ human T cell clone which is specific for residues 307–319 of the hemagglutinin (HA) of influenza virus. NBHAc25 cells were maintained in-vitro in the presence of 50 U of IL-2 in complete medium (RPMI, 10% FCS, 1% antibiotics, 1% L-glutamine) and by biweekly stimulation with the synthetic peptide 307–310.

Dendritic cells were prepared as described with minor modifications (Romani, et al., *J. Exp. Med.* 180: 83–93 (1994)). In brief, isolated PBL were plated onto 6 well plates at 1.5×10$^7$/well. Plates were incubated at 37° C. for two hours after which non-adherent cells were removed by washing with PBS. Adherent cells were cultured in RPMI supplemented with 10% fetal bovine serum containing 800 U recombinant GM-CSF (Pepro Tech, Rocky Hill, N.J.) per ml and 400 U IL-4 (Pepro Tech, Rocky Hill, N.J.) per ml. Medium with cytokines was added at days 3 and 7. Cells were harvested for immunostaining on days 7–10. Typically, dendritic cells were large, bright cells with veils. Cell surface phenotyping indicated positive expression of CD1a, CD13, CD80, CD83, HLA-DR and low or negative expression of CD14 (results not shown).

By immunofluorescent staining the panel of Mabs reacted positively with two human PrP$^c$ neuroblastoma transfectants, expressing either PrP$^c$ with Met (M17-M) at residue 129 or Val (M17-V) at residue 129. Thus, these Mabs do not distinguish between the most common polymorphism found in the human PrP$^c$ gene. All the Mabs also reacted with STT and CRT, two astrocytoma cell lines derived from patients with grade IV astrocytoma.

Figure 7:
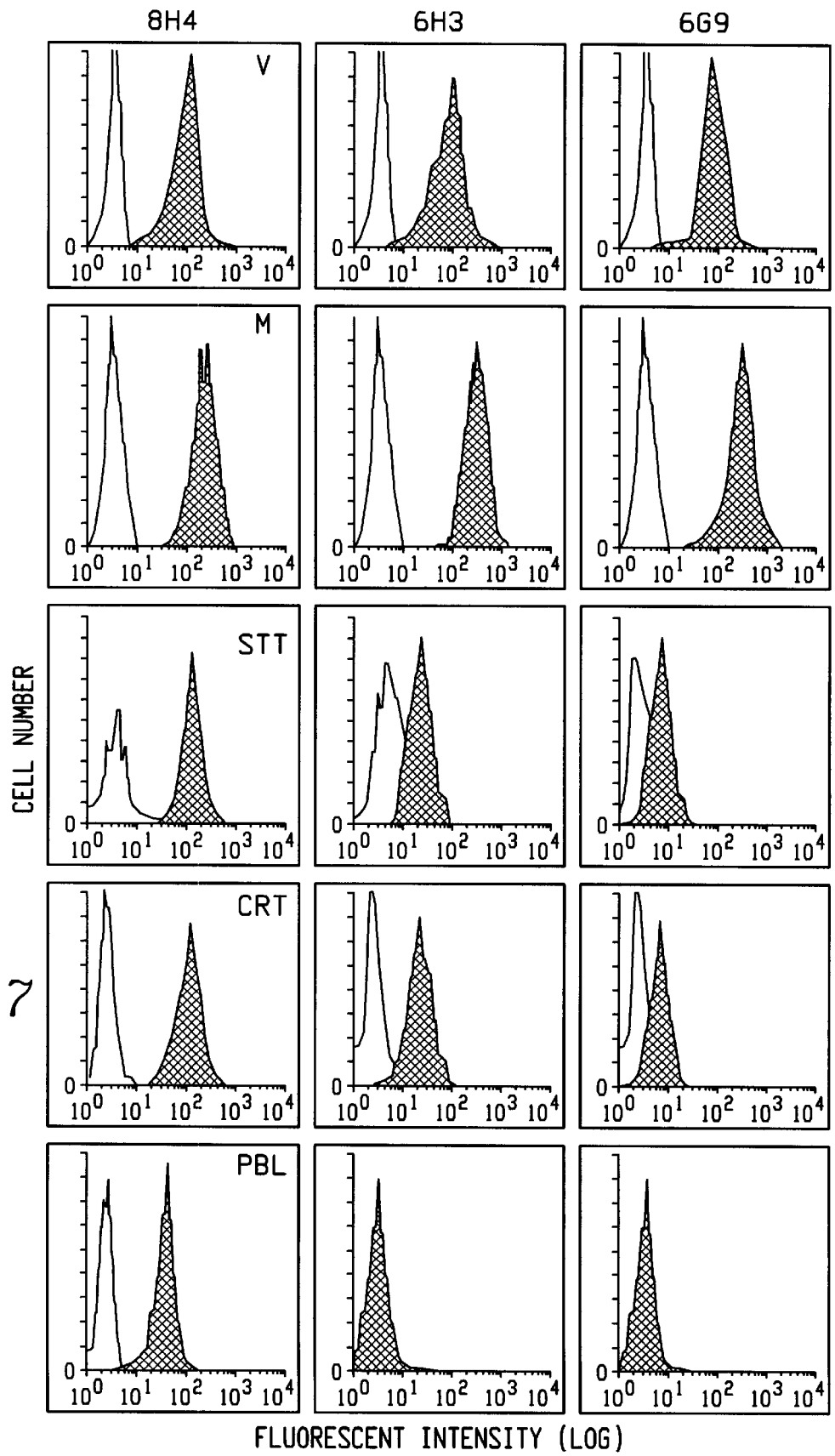
Figure 8:
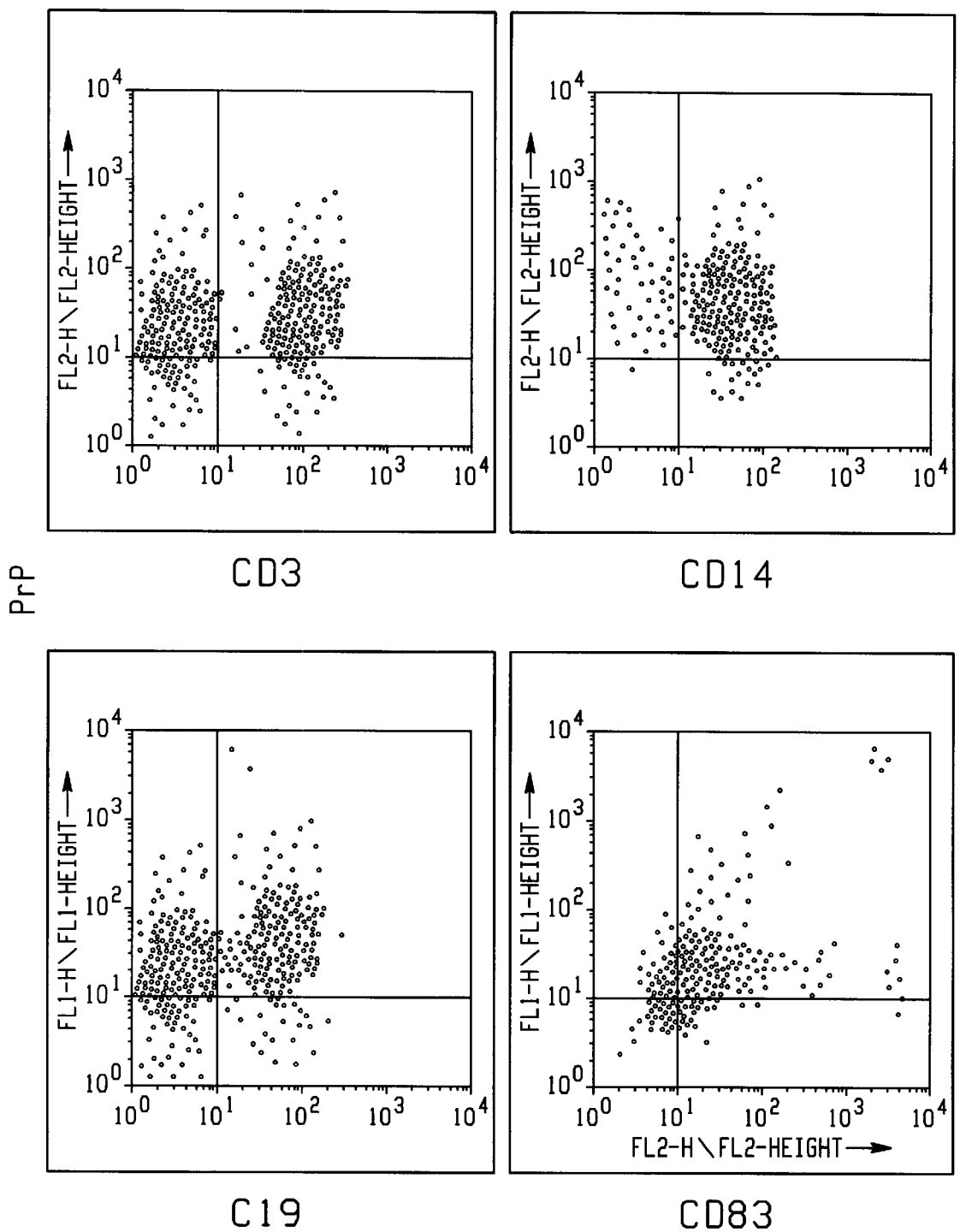
FIG. 8 is a set of four graphs of two-color FACS analysis of PrP bearing CD3 positive T-cells, CD19 positive B-cells, CD14 positive monocytes and CD83 positive dendritic cells in human circulation.

In contrast, staining of human PBL with these Mabs revealed differences in the epitope recognition of these Mabs. Five of the seven Mabs reacted strongly with human PBL, confirming an earlier study demonstrating the presence of PrP$^c$ on human PBL with a polyclonal antisera (Cashman, et al., *Cell* 61: 185–192 (1990)). However, two of the Mabs, 6H3 and 6G9 did not stain human PBL (n=10) (FIG. 7). The lack of 6H3 staining of normal PBL is not due to lower levels of PrP$^c$ expression on PBL. The 6H3 reactive epitope is readily detectable on STT astrocytoma and other tumor cell lines which express either comparable or lower levels of PrP$^c$ than normal PBL (results not shown). These results provide evidence that the PrP$^c$ on human PBL may be qualitatively different from PrP$^c$ transfectants or astrocytomas. Characterization of the cell types expressing PrP$^c$ in PBL was performed by two color flow-cytometry analysis. PrP$^c$ is expressed on CD3$^+$T cells, CD19$^+$B cells, CD14$^+$ monocytes and CD83$^+$ dendritic cells (FIG. 8).

Figure 9:
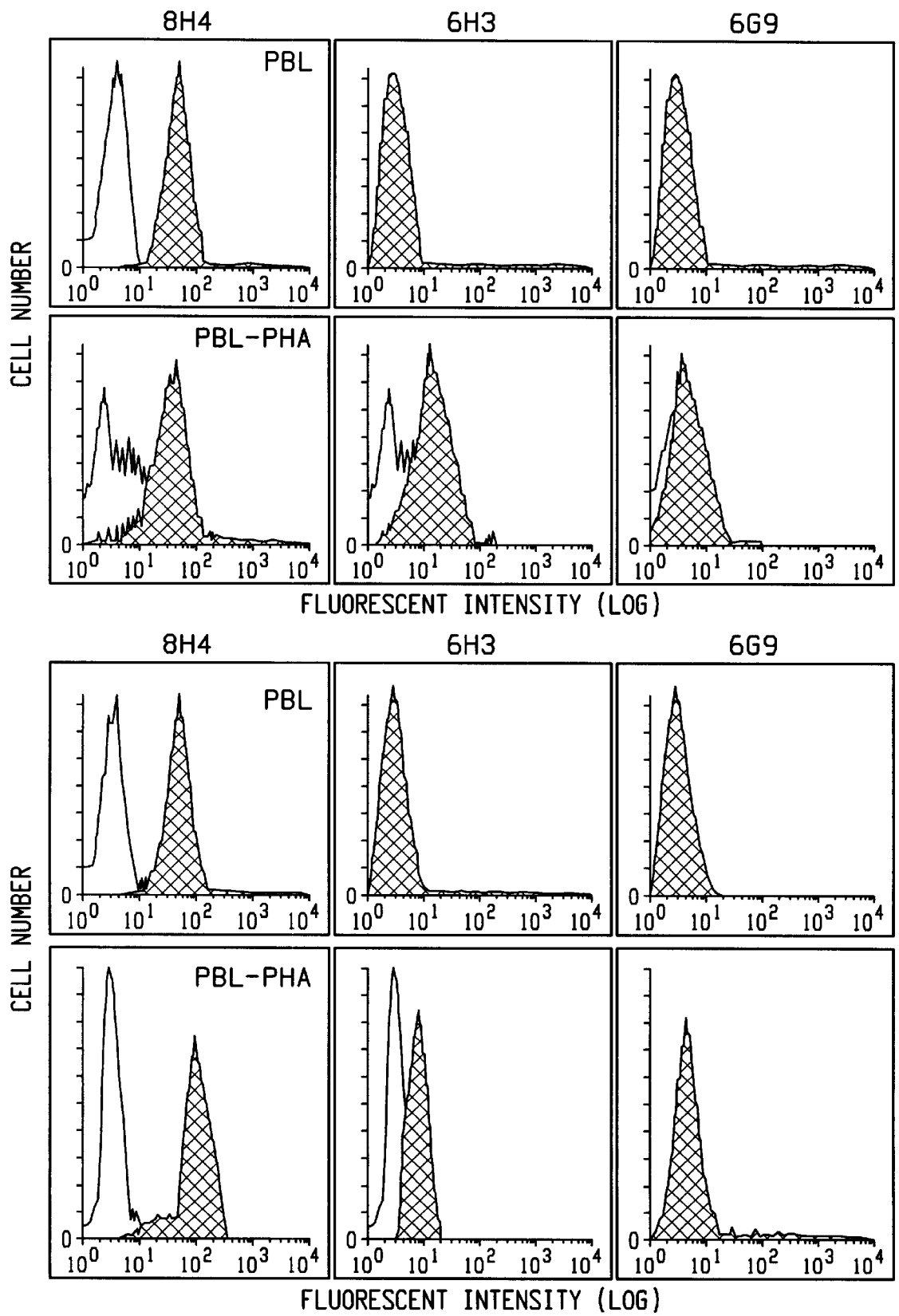
FIG. 9 is a series of graphs, analyzed on FACScan, showing expression of the 6H3 monoclonal antibody present on activated but not normal resting leukocytes from two different donors. Clear areas representing staining profiles with irrelevant IgG$_1$ control antibodies and shaded areas representing staining profiles with anti-PrP Mabs.
Figure 10:
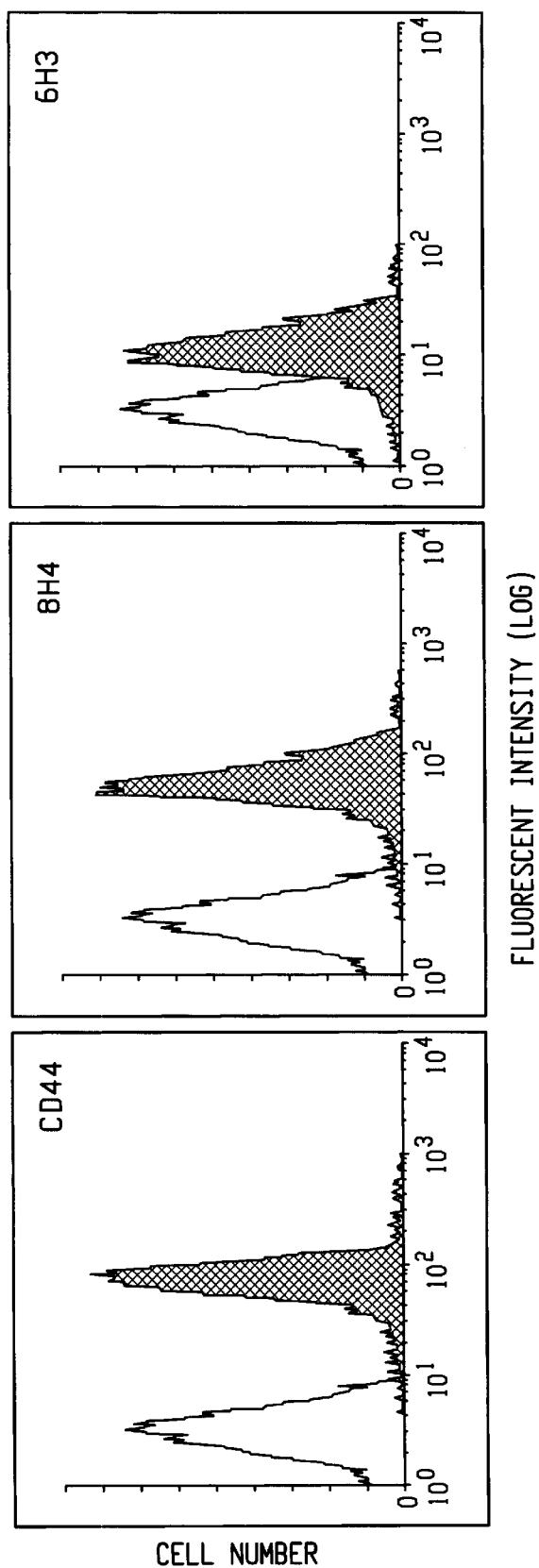
FIG. 10 is a series of graphs showing the Mab 6H3 reacting with an epitope present on a human T cell clone.
Figure 11:
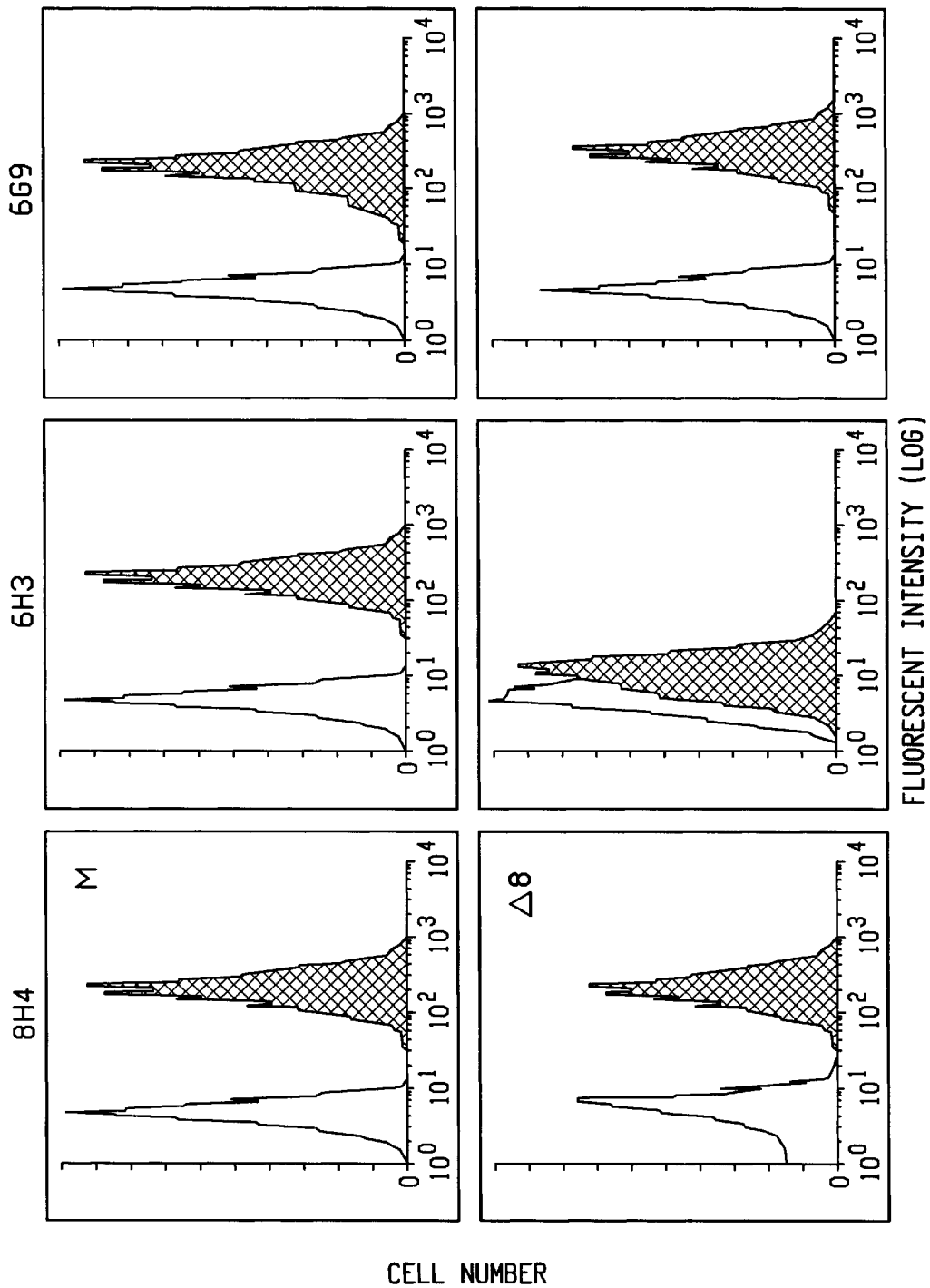
FIG. 11 is a series of graphs showing Mab 6H3 reacting with an epitope that is dependent on the presence of the octapeptide repeat region within the PrP$^c$ protein.

A hint for the location of the Mab 6H3 reactive epitope was provided by the failure of Mab 6H3 to stain a mutant PrP$^c$ neuroblastoma transfectant ($\Delta$8) which expresses a mutated human PrP$^c$ protein that lacks the octapeptide repeats (FIG. 9). The level of mutant PrP protein expressed on the surface of $\Delta$8 is comparable to the wild type transfectant as demonstrated by staining with multiple anti-PrP$^c$ Mabs (FIG. 11). Of the seven Mabs tested, only Mab 6H3 failed to react with $\Delta$8. These results suggest that the epitope recognized by Mab 6H3 is located within the octapeptide repeat region. Alternatively, exposure of the Mab 6H3 epitope may require the presence of the octapeptide repeats. Mab 6H3 did not react with a synthetic peptide including one of the octapeptide repeats (a.a. 82–97) in an ELISA (results not shown). Therefore, if the epitope bound by Mab 6H3 is indeed located in the octapeptide region, it most likely represents a conformational rather than a linear epitope.

B. Immunofluorescent Staining

Human peripheral blood lymphocytes, activated lymphocytes or tumor cell lines were prepared and washed with washing medium (PBS supplemented with 5% newborn calf serum, 0.1% NaN3, pH 7.4). Single cell hsuspensions (1×10$^6$/ml) were incubated with affinity purified Mabs, hybridoma supernatants, or an isotype control antibody on ice for 45 min. Cells were washed three times with washing medium and 25 ul of FITC-conjugated Goat anti-mouse IgG antibody was added and incubated for 45 min. on ice. Finally, samples were washed and fixed with 1% paraformaldehyde. For two color immuno-fluorescence staining, a FITC-anti-CD3, FITC conjugated anti-CD19, FITC conjugated anti-CD14, or FITC conjugated anti-CD83 was incubated with the cells, washed twice, and then stained with a biotinylated anti-PrP$^c$ Mab 8H4. Bound biotinylated 8H4 was detected with PE-conjugated avidin. Cells were analyzed in a FACScan (Becton Dickinson, San Jose, Calif.). At least 5,000 cells were analyzed per sample in all experiments. All experiments were done at least three times.

Since mitogen activation increases susceptibility to prion infection, the effect of T lymphocyte activation on cell surface PrP$^c$ expression was assessed. Activation of PBL from two donors with PHA either did not (FIG. 9, top panel) or slightly up-regulated (FIG. 9, bottom panel) the expression of PrP$^c$ on the cell surface, as detected by immuno-staining with Mab 8H4. Mab 6H3, which normally does not stain unstimulated PBL, reacted positively with activated PBL from both donors. Binding of Mab 6H3 is specific, because another anti-PrP$^c$ Mab, 6G9, stains neither normal PBL nor activated PBL (FIG. 9). Similar results have been obtained with PBL from four additional donors. Of the six donors studied, PHA up-regulated the expression of PrP in four of these donors. The mechanism underlying the differences in up-regulation are unknown. The observation that Mab 6H3 reactive epitope is present on activated T cell is further supported by the findings that Mab 6H3 reacted specifically with an antigen specific human T cell clone, NBHAc25.

Based on these observations, applicants concluded that Mab 8H4 recognizes an epitope on PrP$^c$ that is constitutively expressed on neuroblastoma transfectants, astrocytomas and PBL. In contrast, Mab 6H3 reacts with a PrP$^c$ epitope that is constitutively expressed on neuroblastoma transfectants and astrocytomas, but expression of this epitope on normal PBL requires cellular activation. The PrP$^c$ epitope bound by Mab 6G9 is specific for neuroblastoma transfectants and astrocytomas.

C. Biotinylation, immunoprecipitation and immunoblotting of cell surface PrP and Brain Tissues Normal human brain tissue was prepared using the materials and methods described in Example 2 B, with prestained Mol. Wt. markers used as standards.

Cells were surface labeled using a biotinylation procedure. Briefly, cells (10$^7$/ml) were incubated with sulfosuccinomidobiotin (Pierce Co., Rockford, Ill.) (0.1 mg/ml) in labeling buffer (150 uM NaCl, 0.1 M Hepes, pH 8) for 30 minutes at room temperature. Cells were then washed with RPMI medium supplemented with 3% FCS and lysed with 1% Triton X-100 in 10 mM Tris, pH 7.5, 150 mM NaCl, 3 mM EDTA, 50 mM iodoacetamide, 0.1% NaN$_3$, 1 mM PMSF, 10 ug/ml soybean trypsin inhibitor, 1 ug/ml leupeptin, and 1 U/ml of aprotinin for 1 hour at 40 C. The detergent solubilized materials were recovered after centrifugation and precleared with an irrelevant antibody and Sepharose 4 B beads, followed by immunoprecipitation with anti-PrP$^c$ Mab. After extensive washing, proteins were eluted from beads by boiling in non-reducing SDS sample buffer and analyzed by SDS-PAGE with a 12% gel. Separated proteins were then transferred to a nitrocellulose membrane. The membrane was blocked with 0.5% gelatin in PBS plus 0.05% Tween 20 and 0.05% thimerosal for 1 hour at room temperature. After blocking, membranes were incubated with 1/1000 or 1/500 diluted streptavidin-horseradish peroxidase in PBS containing 1% BSA and 0.05% Tween 20. The protein bands were detected using the enhanced chemiluminescence system (Amersham Corp., Arlington Heights, Ill.). Prestained Mol. Wt. markers were used as standards.

Three major glycoforms of PrP$^c$ are present in normal human brain: the fully-glycosylated 33–42 KDa protein; the intermediately-glycosylated 29 KDa protein; and the unglycosylated 27 KDa protein. In addition a small amount of a truncated 25 KDa prion protein is also present, as described in Example 2A. The composition of the PrP$^c$ in glycoforms in human PBL has not been studied in detail. Applicants compared the expression of the total cellular PrP$^c$ glycoforms in normal human PBL with PrP$^c$ glycoforms in human brain by immuno-blotting with Mab 8H4 (FIG. 12A). In human PBL, both the fully glycosylated and intermediately-glycosylated PrP$^c$ are present. However, the level of unglycosylated 27 KDa protein is significantly reduced and the 25 KDa truncated protein is undetectable (FIG. 12A). When N-linked glycans were removed, all three glycoforms migrated at 27 KDa. In addition, an 18 KDa fragment was identified in both brain tissues and PBL.

The fully glycosylated and intermediately-glycosylated PrP$^c$ in PBL migrated a bit slower than the same glycoforms from the brain. Whether the altered migration is due to differences in the nature of the N-linked glycans on PrP$^c$ in human PBL will require further biochemical studies. Applicants determined the composition of PrP$^c$ glycoforms on the cell surface by surface biotinylation followed by precipitation with Mab 8H4, and then Western blotting with avidin conjugated enzymes. The 27 KDa unglycosylated PrP$^c$ is readily detected on neuroblastoma transfectants (FIG. 12B). In contrast, the 27 KDa unglycosylated protein is undetectable on the surface of human PBL. These observations provide an explanation for the lack of binding of Mab 6G9 to PBL; Mab 6G9 preferentially recognizes the unglycosylated 27 KDa glycoform, as described in Example 2A. These results also provide conclusive biochemical evidence that the composition of PrP$^c$ glycoforms on human lymphocytes is different from that in human brain tissues or human neuroblastoma transfectants.

Repeated attempts to use Mab 6H3 for Western blotting were unsuccessful. Since Mab 6H3 reacts with PrP$^c$ on the cell surface but not with PrP$^c$ under denaturing conditions, as required for Western blotting, the epitope recognized by Mab 6H3 may represent a conformation-dependent epitope of PrP$^c$. We next investigated whether Mab 8H4 and Mab 6H3 react with different PrP$^c$ glycoforms on M17-M transfectants by cell surface biotinylation and immunoprecipitation, instead of Western blotting. Both Mabs 8H4 and 6H3 reacted with the three known prion glycoforms on the cell surface. However, the amount of PrP$^c$ immunoprecipitated with Mab 6H3 was significantly lower, especially the highly glycosylated glycoforms.

Applicants next performed sequential immunoprecipitation experiments with Mab 8H4 and then followed with Mab 6H3, or vice versa. When the M17-V cell lysate was first precleared with Mab 8H4 and then immunoprecipitated with Mab 6H3, only a small smear of highly glycosylated PrP$^c$ glycoforms were detected. In some experiments, three distinct bands can be visualized in this region. Furthermore, both the intermediately and the unglycosylated PrP$^c$ glycoforms are no longer detectable (FIG. 12C). This experiment provides strong evidence that Mab 6H3 preferentially recognizes a small subset of the highly glycosylated PrP$^c$ glycoforms, in addition to the unglycosylated and intermediately-glycosylated PrP$^c$. This subset of PrP$^c$ is not recognized by Mab 8H4. No protein band is present when the Mab 8H4 depleted supernatant was reimmunoprecipitated with Mab 8H4. In contrast, preclearing of the cell lysate with Mab 6H3 did not drastically reduce the total amount of PrP$^c$ glycoforms precipitated by Mab 8H4. These results corroborate our earlier findings that the subset of PrP$^c$ glycoforms recognized by Mab 6H3 represents a very small subset of the PrP$^c$ glycoforms.

Applicants determined whether cellular activation alters the composition of PrP$^c$ glycoforms on the surface of human PBL. Cellular activation did not drastically alter the PrP$^c$ glycoforms found on the cell surface as revealed by immunoprecipitation with Mab 8H4 (FIG. 13A). Mab 6H3 does not immunoprecipitate any specific proteins from normal resting PBL (results not shown). However, both Mabs 8H4 and 6H3 did immunoprecipitate PrP$^c$ on PHA activated PBL (FIG. 13B). As was found using surface labeled M17-V cells, when the 8H4 precleared supernatants were re-immunoprecipitated with Mab 6H3, a small amount of highly glycosylated PrP$^c$ was detected from activated PBL. Pre-clearing with Mab 6H3 slightly reduced the levels of PrP$^c$ immunoprecipitated with Mab 8H4, thus, confirming our finding with neuroblastoma transfectants that Mab 8H4 and 6H3 react with different PrP glycoforms. More importantly, these results suggest that cellular activation may induce the expression of a small subset of PrP$^c$ glycoforms, which are absent on normal lymphocytes. Alternatively, cellular activation may alter the conformation of the PrP$^c$ on lymphocytes and thus render the epitope accessible to Mab 6H3.

Discussion

Using the new panel of Mabs applicants have demonstrated that the PrP$^c$ glycoforms on normal human PBL are different from the PrP$^c$ glycoforms expressed in normal human brain tissue, on astrocytomas or on transfected enuroblastomas. More specifically, applicants provided evidence that human peripheral blood lymphocytes lack the unglycosylated 27 KDa glycoisoform on their surface. Furthermore, the activation of lymphocytes resulted in quantitative as well as qualitative changes in the expression of PrP$^c$. Mab 6H3 reacts only with activated PBL or an antigen specitic T cell clone but not with normal resting PBL.

Applicants observations may assist in explaining why activated lymphocytes are more efficient in prion propagation. First, the level of PrP$^c$ expression determines the progression of prion diseases in transgenic mice. Since activated lymphocytes from some donors express more prion protein they may promote the conversion process by providing more substrate PrP$^c$. Second, conversion from PrP$^c$ to PrP scinvolves multiple intermediate steps, therefore, the conformation of PrP$^c$ on activiated lymphocytes may be more conducive to PrP conversion than PrP$^c$ on normal resting lymphocytes. However, resting lymphocytes may act as a reservoir for pathogenic PrP during the long latency period associated with peripheral routes of infection.

Upon mitogenic activation, up-regulation of PrP expression on PBL was observed in approximately half of the normal donors. The reason PrP$^c$ on some lymphocytes can be up-regulated while not on others is not known. The amino acid 129 polymorphism is common in Caucasian populations; approximately 51% of the Caucasian population is heterozygous at residue 129. Homozygosity at residue 129 either with Met or Val predisposes individuals to infectious, as well as sporadic prion diseases. Experiments are now in progress to determine whether homozygosity at residue 129 plays a role in determining the levels of PrP$^c$ expression on normal or activated lymphocytes.

The exact location of the epitope recognized by Mab 6H3 is not known. It is clear, however, that the Mab 6H3 reactive epitope is located either within the octapeptide repeat region or in another region of the PrP$^c$ with its availability for binding being dependent on the octapeptide repeats. The octapeptide repeat region is extremely flexible and is important in the pathogenesis of some inherited prion diseases. This "plastic" region could feature in the conversion of PrP$^c$ to PrP$^{sc}$ by template-assisted formation of β sheet structure. The Mab 6H3 reactive epitope may represent one of the conformational determinants that promoted PrP$^c$ conversion.

Conversion from PrP$^c$ to PrP has been accomplished in vitro. If Mab 6H3 detects a transitional conformation dependent determinant that is important for the conversion from PrP$^c$ to PrP$^{sc}$, Mab 6H3 may be able to block PrP$^c$ conversion in-vitro or in-vivo. Currently there is no treatment for any form of prion disease. Since Mab 6H3 does not react with PrP on normal lymphocytes, applicants may be able to test whether Mab 6H3 can selectively interfere with prion propagation when infection is initiated via the peripheral route.

The biological significance of the finding that the 27 KDa unglycosylated PrP glycoform is absent on the surface of lymphocytes is not known. The two N-linked glycosylation sites at residues 181 and 197 in human are highly conserved. Variations in glycosylation at these two sites may influence the rate at which $PrP^c$ is converted into $PrP^{sc}$. More recent studies revealed that Mab 6G9 reacts exclusively with $PrP^c$ glycoisoforms which are not glycosylated at residue 181 (results not shown). Therefore, since Mab 6G9 does not react with human PBL, the predominant 29 KDa, monoglycosylated, $PrP^c$ glycoisoforms present on human PBL must be glycosylated at residue 181 rather than 197.

The physiologic functions of PrP on human lymphocytes are not known. Earlier experiments revealed that $PrP^c$ may participate in signal transduction. Addition of the a polyclonal rabbit anti-PrP antisera in vitro inhibited the proliferation of human PBL to a mitogen. Both anti-$PrP^c$ Mabs 8H4 and 6H3 inhibited the proliferation of human PBL when they were stimulated with immobilized anti-CD3 Mab (Sy et al., in preparation).

Therefore, cross-linking of $PrP^c$ on human T cells was able to interfere with signal transduction initiated by the T cell receptor and CD3 complex.

EXAMPLE 4

ELISA for measuring soluble $PrP^c$ in culture supernatant or in circulation

The $PrP^c$ on the cell surface has a relatively short half-life of approximately 3 to 4 hours. This high turn-over rate may be due to the internalization of the $PrP^c$ or shedding of the $PrP^c$. WV is a human neuroblastoma cell line that has been transfected with a human PrP gene. Applicants collected supernatants from the cell line and determined whether they can detect soluble $PrP^c$ in the culture supernatant.

For the ELISA, applicants first coated the plastic plates with affinity purified anti-$PrP^c$ monoclonal antibody 6H3 over night. Different dilutions of the culture supernatant or a control supernatants were added into the plates. Bound $PrP^c$ proteins were detected with a biotinylated anti-$PrP^c$ monoclonal antibody 8H4. The results are shown in FIG. 14. Significant levels of soluble $PrP^c$ can be detected in the supernatant from WV transfectants but not in culture medium alone.

EXAMPLE 5

Anti-PrP Mab 5B2 can distinguish between recombinant normal human $PrP^c$ and a pathogenic mutated PrP (F198S)

Mutation in the human PrP gene resulting in a change from Phe to Ser in amino acid residue 198 is one of the pathogenic mutations that have been identified in patients with inherited prion diseases. Applicants generated a recombinant human prion protein in which residue 198 has been changed from Phe to Ser (F198S). Applicants then investigated whether any of their anti-PrP Mabs could distinguish mutant PrP from wild type PrP proteins.

In this regard, Applicants coated ELISA plates with 10 ug/ml or either normal wild type human recombinant $PrP^c$ with a Met at residue 129 (129M) or with PrP which has a Val at residue 129 or with mutant prion protein, F198S. Different concentrations of Mab 5B2 were used to detect bound PrP proteins. An enzyme conjugated goat antimouse Ig was used to quantify the captured Mab 5B2. Results from a representative experiment are shown in FIG. 15. Mab 5B2 reacted significantly more to F198S prion protein than the two normal PrP proteins. These results provide strong evidence that Mab 5B2 can distinguish mutant prion protein from normal prion protein. These results also provide supportive evidence that an ELISA can be developed to identify and quantify pathogenic prion proteins in patients with prion diseases.

The invention has been described with reference to the preferred embodiments. Obviously, modifications and alterations will occur to others upon reading and understanding the preceding detailed description. It is intended that the invention be call such alternations and modifications insofar as they come within the scope of the claims and the equivalents thereof.

Having thus described the preferred embodiments, the invention is now claimed to be:

1. A method for detecting the amount of mammalian prion protein in a sample comprising the steps of:
   a) preparing a monoclonal antibody 2F8 obtained from hybridoma cell line ATCC PTA-4065 or an epitope binding fragment thereof, which is immunoreactive with prion protein;
   b) bringing said monoclonal antibody or fragment thereto into contact with the sample; and
   c) measuring the amount of antigen-antibody complex formed in the sample, wherein the amount of complex is directly proportional to the amount of prion protein present in the sample.

2. The method of claim 1, wherein said monoclonal antibody or fragment thereto is labeled.

3. A method of detecting prion protein in a sample comprising the steps of:
   a) preparing a monoclonal antibody 2F8 obtained from hybridoma cell line ATCC PTA-4065 or an epitope binding fragment thereto that bind specifically to prion protein;
   b) preparing a second antibody to said monoclonal antibody or fragment thereto;
   c) labeling said second antibody;
   d) adding the monoclonal antibody to the sample;
   e) incubating the sample containing the monoclonal antibody;
   f) adding the second labeled antibody to the sample containing the monoclonal antibody; and,
   g) measuring the antigen-monoclonal antibody-second labeled antibody reaction in said sample.

4. A sandwich immunoassay kit for determining the amount of prion protein in a sample, comprising:
   a) a first container containing a carrier-bound antibody which is immunoreactive with prion protein; and
   b) a second container containing an antibody which is immunoreactive with prion protein and is detectably labeled wherein said first container contains a monoclonal antibody 2F8 obtained from hybridoma cell line ATCC PTA-4065 or fragment thereof, and wherein said second antibody contains the detectable labeled antibody which forms an antibody antigen/antibody ternary complex with said monoclonal antibody and prion protein.

* * * * *